US008815211B2

(12) United States Patent
Hino et al.

(10) Patent No.: US 8,815,211 B2
(45) Date of Patent: Aug. 26, 2014

(54) RADIOACTIVE METAL-LABELED ANTI-CADHERIN ANTIBODY

(75) Inventors: Akihiro Hino, Sammu (JP); Akio Nagano, Sammu (JP); Masahiko Watanabe, Sammu (JP); Tadasi Matsuura, Tokyo (JP); Hirokazu Satoh, Tokyo (JP); Fumiko Nomura, Tokyo (JP); Katsuyuki Mitomo, Tokyo (JP)

(73) Assignees: Fujifilm RI Pharma Co., Ltd., Tokyo (JP); Perseus Proteomics Inc., Tokyo (JP)

( * ) Notice: Subject to any disclaimer, the term of this patent is extended or adjusted under 35 U.S.C. 154(b) by 0 days.

(21) Appl. No.: 13/578,462

(22) PCT Filed: Feb. 9, 2011

(86) PCT No.: PCT/JP2011/052759
§ 371 (c)(1),
(2), (4) Date: Aug. 10, 2012

(87) PCT Pub. No.: WO2011/099524
PCT Pub. Date: Aug. 18, 2011

(65) Prior Publication Data
US 2013/0071324 A1 Mar. 21, 2013

(51) Int. Cl.
*A61K 49/00* (2006.01)
*A61K 39/395* (2006.01)
*C07K 16/00* (2006.01)
*C07K 16/28* (2006.01)

(52) U.S. Cl.
USPC ... 424/9.1; 424/130.1; 424/143.1; 424/144.1; 530/387.1; 530/388.22; 530/391.1; 530/391.3

(58) Field of Classification Search
None
See application file for complete search history.

(56) References Cited

U.S. PATENT DOCUMENTS

| | | | |
|---|---|---|---|
| 2003/0194406 | A1 | 10/2003 | Reinhard et al. |
| 2003/0235534 | A1 | 12/2003 | Griffiths et al. |
| 2006/0039915 | A1 | 2/2006 | Reinhard et al. |
| 2006/0165701 | A1 | 7/2006 | De Haen |
| 2006/0240001 | A1 | 10/2006 | Bauer et al. |
| 2009/0118487 | A1 | 5/2009 | Bauer et al. |
| 2009/0169572 | A1 | 7/2009 | Nakatsuru et al. |
| 2011/0182884 | A1 | 7/2011 | Bauer et al. |
| 2012/0128584 | A1 | 5/2012 | Togashi et al. |
| 2012/0136140 | A1 | 5/2012 | Aburatani et al. |

FOREIGN PATENT DOCUMENTS

| | | | |
|---|---|---|---|
| JP | 2005 522982 | | 8/2005 |
| JP | 2005 532343 | | 10/2005 |
| JP | 2006 509744 | | 3/2006 |
| JP | 2008 538909 | | 11/2008 |
| JP | 2009 528257 | | 8/2009 |
| WO | WO/00/26672 | * | 5/2000 |
| WO | WO 2004/110345 | A2 | 12/2004 |
| WO | WO 2004/110345 | A3 | 12/2004 |
| WO | WO 2005/090572 | A2 | 9/2005 |
| WO | WO 2005/090572 | A3 | 9/2005 |
| WO | WO 2010/001585 | A1 | 1/2010 |

OTHER PUBLICATIONS

Hino et al. Preclinical evaluation of anti-cadherin 3 human-mouse chimeric monoclonal antibody FF-21101 radioimmunotherapy. J Nucl Med. 2013; 54 (Supplement 2):1367.*

Jarrard et al. P-Cadherin is a basal cell-specific epithelial marker that is not expressed in prostate cancer. Clin Cancer Res. Nov. 1997;3(11):2121-8.*

Bloechl, S., et al., "Fractionated Locoregional Low-Dose Radioimmunotherapy Improves Survival in a Mouse Model of Diffuse-Type Gastric Cancer Using a $^{213}$Bi-Conjugated Monoclonal Antibody," Clinical Cancer Research, vol. 11, Suppl. 19, pp. 7070s-7074s, (Oct. 1, 2005).

Jaggi, J.S., et al., "Selective Alpha-Particle Mediated Depletion of Tumor Vasculature with Vascular Normalization," PLoS One, Issue 3, e 267, pp. 1-9, (2007).

Senekowitsch-Schmidtke, R., et al., "Highly Specific Tumor Binding of a $^{213}$Bi-labeled Monoclonal Antibody against Mutant E-Cadherin Suggests Its Usefulness for Locoregional $\alpha$-Radioimmunotherapy of Diffure-Type Gastric Cancer," Cancer Research, vol. 61, pp. 2804-2808, (Apr. 1, 2001).

McDevitt, M.R., et al., "Design and synthesis of $^{225}$Ac radioimmunopharmaceuticals," Applied Radiation and Isotopes, vol. 57, pp. 841-847, (2002).

Saji, H., "Application of Radiometallic Compounds for Medical Diagnosis and Therapy," Yakugaku Zasshi, vol. 128, No. 3, pp. 323-332, (2008) (with English abstract).

Watanabe, T., et al., "Phase I study of radioimmunotherapy with an anti-CD20 murine radioimmunoconjugate ($^{90}$Y-ibritumomab tiuxetan) in relapsed or refractory indolent B-cell lymphoma," Cancer Science, vol. 96, No. 12, pp. 903-910, (Dec. 2005).

International Search Report Issued May 10, 2011 in PCT/JP11/52759 Filed Feb. 9, 2011.

Extended Search Report issued Jun. 10, 2013 in European Application No. 11 74 2267.5.

David M. Goldenberg, "Advancing role of radiolabeled antibodies in the therapy of cancer", Cancer Immunology and Immunotherapy, vol. 52, No. 5, 2003, pp. 281-296.

* cited by examiner

*Primary Examiner* — Maher Haddad
(74) *Attorney, Agent, or Firm* — Oblon, Spivak, McClelland, Maier & Neustadt, L.L.P.

(57) ABSTRACT

An object of the present invention is to provide a radioactive metal anti-cadherin antibody which is highly accumulated specifically in cancer tissue. Another object is to provide a cancer therapeutic agent having high anti-cancer effect and safety and a cancer diagnostic agent. The radioactive metal-labeled anti-cadherin antibody is obtained by binding a radioactive metallic element to an anti-cadherin antibody via a metal-chelating reagent.

24 Claims, 14 Drawing Sheets

SEQUENCE LISTING

<160> NUMBER OF SEQ ID NOS: 47

<210> SEQ ID NO 1
<211> LENGTH: 2490
<212> TYPE: DNA
<213> ORGANISM: Homo sapiens
<220> FEATURE:
<221> NAME/KEY: CDS
<222> LOCATION: (1)..(2490)
<223> OTHER INFORMATION: Homo sapiens

<400> SEQUENCE: 1

```
atg ggg ctc cct cgt gga cct ctc gcg tct ctc ctc ctt ctc cag gtt       48
Met Gly Leu Pro Arg Gly Pro Leu Ala Ser Leu Leu Leu Leu Gln Val
1               5                   10                  15

tgc tgg ctg cag tgc gcg gcc tcc gag ccg tgc cgg gcg gtc ttc agg       96
Cys Trp Leu Gln Cys Ala Ala Ser Glu Pro Cys Arg Ala Val Phe Arg
            20                  25                  30

gag gct gaa gtg acc ttg gag gcg gga ggc gcg gag cag gag ccc ggc      144
Glu Ala Glu Val Thr Leu Glu Ala Gly Gly Ala Glu Gln Glu Pro Gly
        35                  40                  45

cag gcg ctg ggg aaa gta ttc atg ggc tgc cct ggg caa gag cca gct      192
Gln Ala Leu Gly Lys Val Phe Met Gly Cys Pro Gly Gln Glu Pro Ala
    50                  55                  60

ctg ttt agc act gat aat gat gac ttc act gtg cgg aat ggc gag aca      240
Leu Phe Ser Thr Asp Asn Asp Asp Phe Thr Val Arg Asn Gly Glu Thr
65                  70                  75                  80

gtc cag gaa aga agg tca ctg aag gaa agg aat cca ttg aag atc ttc      288
Val Gln Glu Arg Arg Ser Leu Lys Glu Arg Asn Pro Leu Lys Ile Phe
                85                  90                  95

cca tcc aaa cgt atc tta cga aga cac aag aga gat tgg gtg gtt gct      336
Pro Ser Lys Arg Ile Leu Arg Arg His Lys Arg Asp Trp Val Val Ala
            100                 105                 110

cca ata tct gtc cct gaa aat ggc aag ggt ccc ttc ccc cag aga ctg      384
Pro Ile Ser Val Pro Glu Asn Gly Lys Gly Pro Phe Pro Gln Arg Leu
        115                 120                 125

aat cag ctc aag tct aat aaa gat aga gac acc aag att ttc tac agc      432
Asn Gln Leu Lys Ser Asn Lys Asp Arg Asp Thr Lys Ile Phe Tyr Ser
    130                 135                 140

atc acg ggg ccg ggg gca gac agc ccc cct gag ggt gtc ttc gct gta      480
Ile Thr Gly Pro Gly Ala Asp Ser Pro Pro Glu Gly Val Phe Ala Val
145                 150                 155                 160

gag aag gag aca ggc tgg ttg ttg ttg aat aag cca ctg gac cgg gag      528
Glu Lys Glu Thr Gly Trp Leu Leu Leu Asn Lys Pro Leu Asp Arg Glu
                165                 170                 175

gag att gcc aag tat gag ctc ttt ggc cac gct gtg tca gag aat ggt      576
Glu Ile Ala Lys Tyr Glu Leu Phe Gly His Ala Val Ser Glu Asn Gly
            180                 185                 190

gcc tca gtg gag gac ccc atg aac atc tcc atc atc gtg acc gac cag      624
Ala Ser Val Glu Asp Pro Met Asn Ile Ser Ile Ile Val Thr Asp Gln
        195                 200                 205

aat gac cac aag ccc aag ttt acc cag gac acc ttc cga ggg agt gtc      672
Asn Asp His Lys Pro Lys Phe Thr Gln Asp Thr Phe Arg Gly Ser Val
    210                 215                 220

tta gag gga gtc cta cca ggt act tct gtg atg cag gtg aca gcc acg      720
Leu Glu Gly Val Leu Pro Gly Thr Ser Val Met Gln Val Thr Ala Thr
225                 230                 235                 240

gat gag gat gat gcc atc tac acc tac aat ggg gtg gtt gct tac tcc      768
Asp Glu Asp Asp Ala Ile Tyr Thr Tyr Asn Gly Val Val Ala Tyr Ser
                245                 250                 255

atc cat agc caa gaa cca aag gac cca cac gac ctc atg ttc acc att      816
```

-continued

```
Ile His Ser Gln Glu Pro Lys Asp Pro His Asp Leu Met Phe Thr Ile
            260                 265                 270

cac cgg agc aca ggc acc atc agc gtc atc tcc agt ggc ctg gac cgg      864
His Arg Ser Thr Gly Thr Ile Ser Val Ile Ser Ser Gly Leu Asp Arg
        275                 280                 285

gaa aaa gtc cct gag tac aca ctg acc atc cag gcc aca gac atg gat      912
Glu Lys Val Pro Glu Tyr Thr Leu Thr Ile Gln Ala Thr Asp Met Asp
    290                 295                 300

ggg gac ggc tcc acc acc acg gca gtg gca gta gtg gag atc ctt gat      960
Gly Asp Gly Ser Thr Thr Thr Ala Val Ala Val Val Glu Ile Leu Asp
305                 310                 315                 320

gcc aat gac aat gct ccc atg ttt gac ccc cag aag tac gag gcc cat     1008
Ala Asn Asp Asn Ala Pro Met Phe Asp Pro Gln Lys Tyr Glu Ala His
                325                 330                 335

gtg cct gag aat gca gtg ggc cat gag gtg cag agg ctg acg gtc act     1056
Val Pro Glu Asn Ala Val Gly His Glu Val Gln Arg Leu Thr Val Thr
            340                 345                 350

gat ctg gac gcc ccc aac tca cca gcg tgg cgt gcc acc tac ctt atc     1104
Asp Leu Asp Ala Pro Asn Ser Pro Ala Trp Arg Ala Thr Tyr Leu Ile
        355                 360                 365

atg ggc ggt gac gac ggg gac cat ttt acc atc acc acc cac cct gag     1152
Met Gly Gly Asp Asp Gly Asp His Phe Thr Ile Thr Thr His Pro Glu
    370                 375                 380

agc aac cag ggc atc ctg aca acc agg aag ggt ttg gat ttt gag gcc     1200
Ser Asn Gln Gly Ile Leu Thr Thr Arg Lys Gly Leu Asp Phe Glu Ala
385                 390                 395                 400

aaa aac cag cac acc ctg tac gtt gaa gtg acc aac gag gcc cct ttt     1248
Lys Asn Gln His Thr Leu Tyr Val Glu Val Thr Asn Glu Ala Pro Phe
                405                 410                 415

gtg ctg aag ctc cca acc tcc aca gcc acc ata gtg gtc cac gtg gag     1296
Val Leu Lys Leu Pro Thr Ser Thr Ala Thr Ile Val Val His Val Glu
            420                 425                 430

gat gtg aat gag gca cct gtg ttt gtc cca ccc tcc aaa gtc gtt gag     1344
Asp Val Asn Glu Ala Pro Val Phe Val Pro Pro Ser Lys Val Val Glu
        435                 440                 445

gtc cag gag ggc atc ccc act ggg gag cct gtg tgt gtc tac act gca     1392
Val Gln Glu Gly Ile Pro Thr Gly Glu Pro Val Cys Val Tyr Thr Ala
    450                 455                 460

gaa gac cct gac aag gag aat caa aag atc agc tac cgc atc ctg aga     1440
Glu Asp Pro Asp Lys Glu Asn Gln Lys Ile Ser Tyr Arg Ile Leu Arg
465                 470                 475                 480

gac cca gca ggg tgg cta gcc atg gac cca gac agt ggg cag gtc aca     1488
Asp Pro Ala Gly Trp Leu Ala Met Asp Pro Asp Ser Gly Gln Val Thr
                485                 490                 495

gct gtg ggc acc ctc gac cgt gag gat gag cag ttt gtg agg aac aac     1536
Ala Val Gly Thr Leu Asp Arg Glu Asp Glu Gln Phe Val Arg Asn Asn
            500                 505                 510

atc tat gaa gtc atg gtc ttg gcc atg gac aat gga agc cct ccc acc     1584
Ile Tyr Glu Val Met Val Leu Ala Met Asp Asn Gly Ser Pro Pro Thr
        515                 520                 525

act ggc acg gga acc ctt ctg cta aca ctg att gat gtc aat gac cat     1632
Thr Gly Thr Gly Thr Leu Leu Leu Thr Leu Ile Asp Val Asn Asp His
    530                 535                 540

ggc cca gtc cct gag ccc cgt cag atc acc atc tgc aac caa agc cct     1680
Gly Pro Val Pro Glu Pro Arg Gln Ile Thr Ile Cys Asn Gln Ser Pro
545                 550                 555                 560

gtg cgc cag gtg ctg aac atc acg gac aag gac ctg tct ccc cac acc     1728
Val Arg Gln Val Leu Asn Ile Thr Asp Lys Asp Leu Ser Pro His Thr
                565                 570                 575
```

-continued

```
tcc cct ttc cag gcc cag ctc aca gat gac tca gac atc tac tgg acg      1776
Ser Pro Phe Gln Ala Gln Leu Thr Asp Asp Ser Asp Ile Tyr Trp Thr
            580                 585                 590

gca gag gtc aac gag gaa ggt gac aca gtg gtc ttg tcc ctg aag aag      1824
Ala Glu Val Asn Glu Glu Gly Asp Thr Val Val Leu Ser Leu Lys Lys
        595                 600                 605

ttc ctg aag cag gat aca tat gac gtg cac ctt tct ctg tct gac cat      1872
Phe Leu Lys Gln Asp Thr Tyr Asp Val His Leu Ser Leu Ser Asp His
    610                 615                 620

ggc aac aaa gag cag ctg acg gtg atc agg gcc act gtg tgc gac tgc      1920
Gly Asn Lys Glu Gln Leu Thr Val Ile Arg Ala Thr Val Cys Asp Cys
625                 630                 635                 640

cat ggc cat gtc gaa acc tgc cct gga ccc tgg aag gga ggt ttc atc      1968
His Gly His Val Glu Thr Cys Pro Gly Pro Trp Lys Gly Gly Phe Ile
            645                 650                 655

ctc cct gtg ctg ggg gct gtc ctg gct ctg ctg ttc ctc ctg ctg gtg      2016
Leu Pro Val Leu Gly Ala Val Leu Ala Leu Leu Phe Leu Leu Leu Val
            660                 665                 670

ctg ctt ttg ttg gtg aga aag aag cgg aag atc aag gag ccc ctc cta      2064
Leu Leu Leu Leu Val Arg Lys Lys Arg Lys Ile Lys Glu Pro Leu Leu
        675                 680                 685

ctc cca gaa gat gac acc cgt gac aac gtc ttc tac tat ggc gaa gag      2112
Leu Pro Glu Asp Asp Thr Arg Asp Asn Val Phe Tyr Tyr Gly Glu Glu
    690                 695                 700

ggg ggt ggc gaa gag gac cag gac tat gac atc acc cag ctc cac cga      2160
Gly Gly Gly Glu Glu Asp Gln Asp Tyr Asp Ile Thr Gln Leu His Arg
705                 710                 715                 720

ggt ctg gag gcc agg ccg gag gtg gtt ctc cgc aat gac gtg gca cca      2208
Gly Leu Glu Ala Arg Pro Glu Val Val Leu Arg Asn Asp Val Ala Pro
            725                 730                 735

acc atc atc ccg aca ccc atg tac cgt cct cgg cca gcc aac cca gat      2256
Thr Ile Ile Pro Thr Pro Met Tyr Arg Pro Arg Pro Ala Asn Pro Asp
            740                 745                 750

gaa atc ggc aac ttt ata att gag aac ctg aag gcg gct aac aca gac      2304
Glu Ile Gly Asn Phe Ile Ile Glu Asn Leu Lys Ala Ala Asn Thr Asp
        755                 760                 765

ccc aca gcc ccg ccc tac gac acc ctc ttg gtg ttc gac tat gag ggc      2352
Pro Thr Ala Pro Pro Tyr Asp Thr Leu Leu Val Phe Asp Tyr Glu Gly
    770                 775                 780

agc ggc tcc gac gcc gcg tcc ctg agc tcc ctc acc tcc tcc gcc tcc      2400
Ser Gly Ser Asp Ala Ala Ser Leu Ser Ser Leu Thr Ser Ser Ala Ser
785                 790                 795                 800

gac caa gac caa gat tac gat tat ctg aac gag tgg ggc agc cgc ttc      2448
Asp Gln Asp Gln Asp Tyr Asp Tyr Leu Asn Glu Trp Gly Ser Arg Phe
            805                 810                 815

aag aag ctg gca gac atg tac ggt ggc ggg gag gac gac tag              2490
Lys Lys Leu Ala Asp Met Tyr Gly Gly Gly Glu Asp Asp
            820                 825


<210> SEQ ID NO 2
<211> LENGTH: 829
<212> TYPE: PRT
<213> ORGANISM: Homo sapiens

<400> SEQUENCE: 2

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
```

-continued

```
        35                  40                  45

Gln Ala Leu Gly Lys Val Phe Met Gly Cys Pro Gly Gln Glu Pro Ala
    50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
    210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
    290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
    370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
    450                 455                 460
```

-continued

```
Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
        515                 520                 525

Thr Gly Thr Gly Thr Leu Leu Leu Thr Leu Ile Asp Val Asn Asp His
    530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
        595                 600                 605

Phe Leu Lys Gln Asp Thr Tyr Asp Val His Leu Ser Leu Ser Asp His
    610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655

Leu Pro Val Leu Gly Ala Val Leu Ala Leu Leu Phe Leu Leu Leu Val
            660                 665                 670

Leu Leu Leu Leu Val Arg Lys Lys Arg Lys Ile Lys Glu Pro Leu Leu
        675                 680                 685

Leu Pro Glu Asp Asp Thr Arg Asp Asn Val Phe Tyr Tyr Gly Glu Glu
    690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
        755                 760                 765

Pro Thr Ala Pro Pro Tyr Asp Thr Leu Leu Val Phe Asp Tyr Glu Gly
    770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825


<210> SEQ ID NO 3
<211> LENGTH: 24
<212> TYPE: DNA
<213> ORGANISM: Artificial sequence
<220> FEATURE:
<223> OTHER INFORMATION: Designed DNA based on CDH3 gene

<400> SEQUENCE: 3
```

-continued

```
cgcggtacca tggggctccc tcgt                                          24


<210> SEQ ID NO 4
<211> LENGTH: 29
<212> TYPE: DNA
<213> ORGANISM: Artificial sequence
<220> FEATURE:
<223> OTHER INFORMATION: Designed DNA based on CDH3 gene

<400> SEQUENCE: 4

ccgtctagat aacctccctt ccagggtcc                                     29


<210> SEQ ID NO 5
<211> LENGTH: 20
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 5

gayatccagc tgactcagcc                                               20


<210> SEQ ID NO 6
<211> LENGTH: 20
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 6

gayattgttc tcwcccagtc                                               20


<210> SEQ ID NO 7
<211> LENGTH: 20
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 7

gayattgtgm tmactcagtc                                               20


<210> SEQ ID NO 8
<211> LENGTH: 20
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 8

gayattgtgy tracacagtc                                               20


<210> SEQ ID NO 9
<211> LENGTH: 20
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 9

gayattgtra tgacmcagtc                                               20
```

<210> SEQ ID NO 10
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 10
gayattmaga tramccagtc 20

<210> SEQ ID NO 11
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 11
gayattcaga tgaydcagtc 20

<210> SEQ ID NO 12
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 12
gayatycaga tgacacagac 20

<210> SEQ ID NO 13
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 13
gayattgttc tcawccagtc 20

<210> SEQ ID NO 14
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 14
gayattgwgc tsacccaatc 20

<210> SEQ ID NO 15
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 15
gayattstra tgacccartc 20

-continued

<210> SEQ ID NO 16
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 16
gayrttktga tgacccarac 20

<210> SEQ ID NO 17
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 17
gayattgtga tgacbcagkc 20

<210> SEQ ID NO 18
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 18
gayattgtga taacycagga 20

<210> SEQ ID NO 19
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 19
gayattgtga tgacccagwt 20

<210> SEQ ID NO 20
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 20
gayattgtga tgacacaacc 20

<210> SEQ ID NO 21
<211> LENGTH: 20
<212> TYPE: DNA
<213> ORGANISM: Artificial sequence
<220> FEATURE:
<223> OTHER INFORMATION: Designed primer based on anti-CDH3 antibody gene

<400> SEQUENCE: 21
gayattttgc tgactcagtc 20

<210> SEQ ID NO 22
<211> LENGTH: 21
<212> TYPE: DNA
<213> ORGANISM: Artificial sequence
<220> FEATURE:
<223> OTHER INFORMATION: Designed primer based on anti-CDH3 antibody gene

<400> SEQUENCE: 22
ggsaccaarc tggaaatmaa a 21

<210> SEQ ID NO 23
<211> LENGTH: 21
<212> TYPE: DNA
<213> ORGANISM: Artificial sequence
<220> FEATURE:
<223> OTHER INFORMATION: Designed primer based on anti-CDH3 antibody gene

<400> SEQUENCE: 23
gggacaaagt tggaaataaa a 21

<210> SEQ ID NO 24
<211> LENGTH: 21
<212> TYPE: DNA
<213> ORGANISM: Artificial sequence
<220> FEATURE:
<223> OTHER INFORMATION: Designed primer based on anti-CDH3 antibody gene

<400> SEQUENCE: 24
gggaccaagc tggagctgaa a 21

<210> SEQ ID NO 25
<211> LENGTH: 24
<212> TYPE: DNA
<213> ORGANISM: Artificial sequence
<220> FEATURE:
<223> OTHER INFORMATION: Designed primer based on anti-CDH3 antibody gene

<400> SEQUENCE: 25
atgragwcac akwcycaggt cttt 24

<210> SEQ ID NO 26
<211> LENGTH: 25
<212> TYPE: DNA
<213> ORGANISM: Artificial sequence
<220> FEATURE:
<223> OTHER INFORMATION: Designed primer based on anti-CDH3 antibody gene

<400> SEQUENCE: 26
atggagacag acacactcct gctat 25

<210> SEQ ID NO 27
<211> LENGTH: 29
<212> TYPE: DNA
<213> ORGANISM: Artificial sequence
<220> FEATURE:
<223> OTHER INFORMATION: Designed primer based on anti-CDH3 antibody gene

<400> SEQUENCE: 27
atggagwcag acacactsct gytatgggt 29

<210> SEQ ID NO 28

<211> LENGTH: 32
<212> TYPE: DNA
<213> ORGANISM: Artificial sequence
<220> FEATURE:
<223> OTHER INFORMATION: Designed primer based on anti-CDH3 antibody
gene
<220> FEATURE:
<221> NAME/KEY: misc_feature
<222> LOCATION: (27)..(27)
<223> OTHER INFORMATION: n at position 27 is i

<400> SEQUENCE: 28
atgaggrccc ctgctcagwt tyttggnwtc tt 32

<210> SEQ ID NO 29
<211> LENGTH: 31
<212> TYPE: DNA
<213> ORGANISM: Artificial sequence
<220> FEATURE:
<223> OTHER INFORMATION: Designed primer based on anti-CDH3 antibody
gene

<400> SEQUENCE: 29
atgggcwtca agatgragtc acakwyycwg g 31

<210> SEQ ID NO 30
<211> LENGTH: 29
<212> TYPE: DNA
<213> ORGANISM: Artificial sequence
<220> FEATURE:
<223> OTHER INFORMATION: Designed primer based on anti-CDH3 antibody
gene

<400> SEQUENCE: 30
atgagtgtgc ycactcaggt cctggsgtt 29

<210> SEQ ID NO 31
<211> LENGTH: 31
<212> TYPE: DNA
<213> ORGANISM: Artificial sequence
<220> FEATURE:
<223> OTHER INFORMATION: Designed primer based on anti-CDH3 antibody
gene

<400> SEQUENCE: 31
atgtggggay cgktttyamm cttttcaatt g 31

<210> SEQ ID NO 32
<211> LENGTH: 28
<212> TYPE: DNA
<213> ORGANISM: Artificial sequence
<220> FEATURE:
<223> OTHER INFORMATION: Designed primer based on anti-CDH3 antibody
gene

<400> SEQUENCE: 32
atggaagccc cagctcagct tctcttcc 28

<210> SEQ ID NO 33
<211> LENGTH: 26
<212> TYPE: DNA
<213> ORGANISM: Artificial sequence
<220> FEATURE:
<223> OTHER INFORMATION: Designed primer based on anti-CDH3 antibody
gene
<220> FEATURE:
<221> NAME/KEY: misc_feature
<222> LOCATION: (6)..(6)
<223> OTHER INFORMATION: n at position 6 is i
<220> FEATURE:
<221> NAME/KEY: misc_feature
<222> LOCATION: (12)..(12)
<223> OTHER INFORMATION: n at position 12 is i
<220> FEATURE:
<221> NAME/KEY: misc_feature
<222> LOCATION: (18)..(18)
<223> OTHER INFORMATION: n at position 18 is i

<400> SEQUENCE: 33
atgagnmmkt cnmttcantt cytggg 26

<210> SEQ ID NO 34
<211> LENGTH: 26
<212> TYPE: DNA
<213> ORGANISM: Artificial sequence
<220> FEATURE:
<223> OTHER INFORMATION: Designed primer based on anti-CDH3 antibody gene
<220> FEATURE:
<221> NAME/KEY: misc_feature
<222> LOCATION: (12)..(12)
<223> OTHER INFORMATION: n at position 12 is i
<220> FEATURE:
<221> NAME/KEY: misc_feature
<222> LOCATION: (24)..(24)
<223> OTHER INFORMATION: n at position 24 is i

<400> SEQUENCE: 34
atgakgthcy cngctcagyt yctnrg 26

<210> SEQ ID NO 35
<211> LENGTH: 25
<212> TYPE: DNA
<213> ORGANISM: Artificial sequence
<220> FEATURE:
<223> OTHER INFORMATION: Designed primer based on anti-CDH3 antibody gene

<400> SEQUENCE: 35
atggtrtccw casctcagtt ccttg 25

<210> SEQ ID NO 36
<211> LENGTH: 27
<212> TYPE: DNA
<213> ORGANISM: Artificial sequence
<220> FEATURE:
<223> OTHER INFORMATION: Designed primer based on anti-CDH3 antibody gene

<400> SEQUENCE: 36
atgtatatat gtttgttgtc tatttct 27

<210> SEQ ID NO 37
<211> LENGTH: 29
<212> TYPE: DNA
<213> ORGANISM: Artificial sequence
<220> FEATURE:
<223> OTHER INFORMATION: Designed primer based on anti-CDH3 antibody gene

<400> SEQUENCE: 37
atgaagttgc ctgttaggct gttggtgct 29

<210> SEQ ID NO 38
<211> LENGTH: 29
<212> TYPE: DNA
<213> ORGANISM: Artificial sequence
<220> FEATURE:

-continued

<223> OTHER INFORMATION: Designed primer based on anti-CDH3 antibody
      gene

<400> SEQUENCE: 38
atggatttwc argtgcagat twtcagctt 29

<210> SEQ ID NO 39
<211> LENGTH: 27
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 39
atggtyctya tvtccttgct gttctgg 27

<210> SEQ ID NO 40
<211> LENGTH: 27
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 40
atggtyctya tvttrctgct gctatgg 27

<210> SEQ ID NO 41
<211> LENGTH: 21
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 41
actggatggt gggaagatgg a 21

<210> SEQ ID NO 42
<211> LENGTH: 26
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 42
atggratgsa gctgkgtmat sctctt 26

<210> SEQ ID NO 43
<211> LENGTH: 26
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 43
atgracttcg ggytgagctk ggtttt 26

<210> SEQ ID NO 44
<211> LENGTH: 25
<212> TYPE: DNA
<213> ORGANISM: Artificial sequence
<220> FEATURE:
<223> OTHER INFORMATION: Designed primer based on anti-CDH3 antibody -continued

```
      gene

<400> SEQUENCE: 44

atggctgtct tggggctgct cttct                                     25


<210> SEQ ID NO 45
<211> LENGTH: 18
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 45

atggrcagrc ttacwtyy                                             18


<210> SEQ ID NO 46
<211> LENGTH: 23
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 46

saggtsmarc tksagsagtc wgg                                       23


<210> SEQ ID NO 47
<211> LENGTH: 19
<212> TYPE: DNA
<213> ORGANISM: Artificial sequence
<220> FEATURE:
<223> OTHER INFORMATION: Designed primer based on anti-CDH3 antibody
      gene

<400> SEQUENCE: 47

casccccatc dgtctatcc                                            19
```

RADIOACTIVE METAL-LABELED ANTI-CADHERIN ANTIBODY

This application is a National Stage of PCT/JP11/052759 filed Feb. 9, 2011 and claims the benefit of JP 2010-028028 filed Feb. 10, 2010.

TECHNICAL FIELD

The present invention relates to a radioactive metal-labeled anti-cadherin antibody which highly specifically accumulates in cancer cells, and to a cancer therapeutic agent and a cancer diagnostic agent each containing the antibody.

BACKGROUND ART

There is keen demand for new cancer therapy for the treatment of cancer, which is now the leading cause of death. Currently, cancer therapies such as surgical therapy, radiotherapy, and chemotherapy (by use of an anti-cancer agent) are employed. Even after surgery, an anti-cancer agent is employed in postoperative therapy.

Currently employed anti-cancer agents include an alkylating agent, an antimetabolite, an alkaloide anti-cancer agent, an antibiotic anti-cancer agent, and a platinum agent. The treatment effects of these agents are not completely satisfactory. Some agents are not cancer cell-specific and frequently cause adverse side effects, which is problematic. Under such circumstances, there is demand for development of more effective anti-cancer agents.

Meanwhile, cadherin is a $Ca^{2+}$-dependent adhesion molecule which is expressed on the cell surface. Examples of known cadherin species include classic cadherins such as E cadherin, N cadherin, and P cadherin (CDH3); as well as protocadherin, and desmosomal cadherin. These cadherins are known to bind homophylicly, to form an adherence junction, and to link to the cytoskeletal system (actin filaments) via intracellular catenin and are considered to control cell adhesion by such a mechanism.

In addition to cell adhesion, cadherin is thought to relate to embryogenesis, morphogenesis, synaptogenesis, synaptic plasticity, and infiltration and metastasis of cancer. Thus, an anti-cadherin antibody is reported to be useful for cancer therapy (Patent Documents 1 to 3).

PRIOR ART DOCUMENTS

Patent Documents

Patent Document 1: Japanese Kohyo (PCT) Patent Publication No. 2005-522982

Patent Document 2: Japanese Kohyo (PCT) Patent Publication No. 2008-538909

Patent Document 3: Japanese Kohyo (PCT) Patent Publication No. 2009-528257

SUMMARY OF THE INVENTION

Problems to be Solved by the Invention

However, the anti-cancer effect of the anti-cadherin antibody is not satisfactory, and there has been demand for development of a more potent cancer therapeutic agent.

Thus, an object of the present invention is to provide a radioactive metal-labeled anti-cadherin antibody which can be highly accumulated in cancer tissue. Another object is to provide a cancer therapeutic agent which contains the antibody as an active ingredient and which exhibits high anticancer effect. Still another object is to provide a cancer diagnostic agent which can predict the efficacy of a cancer therapeutic agent and confirm the therapeutic effect thereof.

Means for Solving the Problems

The present inventors have conducted extensive studies to attain the aforementioned objects, and have found that a radioactive metal-labeled anti-cadherin antibody in which a radioactive metallic element is bound to a anti-cadherin antibody via a metal-chelating reagent is accumulated specifically in the cancer tissue of a cancer-bearing animal, and that the anti-cancer effect thereof is particularly remarkably enhanced as compared to the unlabeled anti-cadherin antibody-administration group. The present invention has been accomplished on the basis of these findings.

Accordingly, the present invention provides a radioactive metal-labeled anti-cadherin antibody which is obtained by binding a radioactive metallic element to an anti-cadherin antibody via a metal-chelating reagent, and a cancer therapeutic agent and a cancer diagnostic agent each containing, as an active ingredient, the radioactive metal-labeled anti-cadherin antibody.

The present invention also provides the radioactive metal-labeled anti-cadherin antibody for use in the treatment or diagnosis of cancer.

The present invention also provides use of the radioactive metal-labeled anti-cadherin antibody for producing a cancer therapeutic agent or a cancer diagnostic agent.

The present invention also provides a method for the treatment or diagnosis of cancer, containing administering an effective amount of the radioactive metal-labeled anti-cadherin antibody to a subject in need thereof.

Effects of the Invention

The cancer therapeutic agent containing, as an active ingredient, the radioactive metal-labeled anti-cadherin antibody of the present invention is highly accumulated in cancer tissue and exhibits high cancer tissue-shrinking effect. Therefore, by use of the cancer therapeutic agent, cancer therapy can be effectively performed without causing adverse side effects. Also, by use of the cancer diagnostic agent of the present invention, the efficacy of the cancer therapeutic agent of the present invention can be predicted, and the therapeutic effect thereof can be confirmed.

MODES FOR CARRYING OUT THE INVENTION

Figure 1:
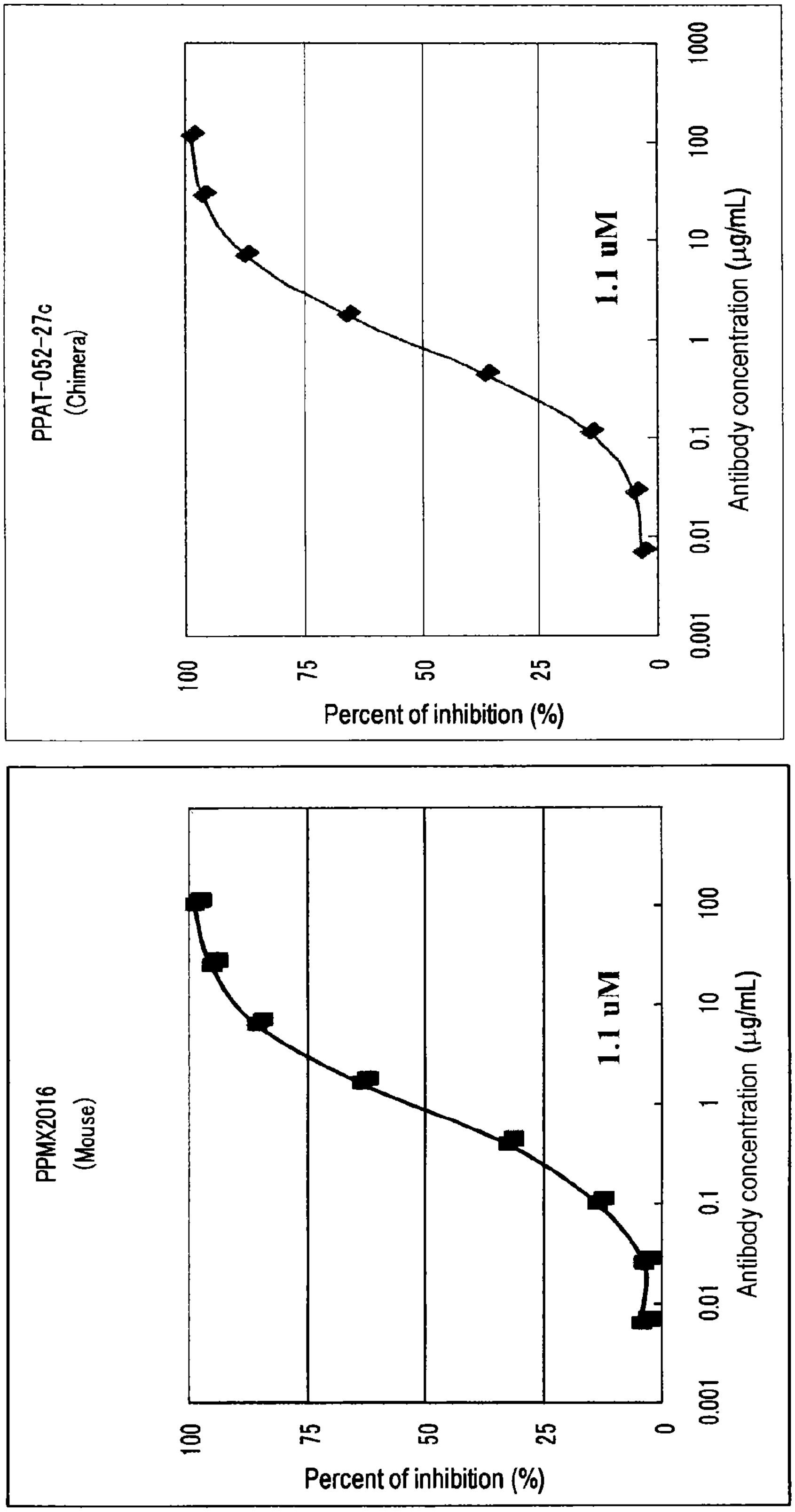
[FIG. 1] Graphs showing the result of the affinity of antibodies evaluated by flow cytometry.
Figure 2:
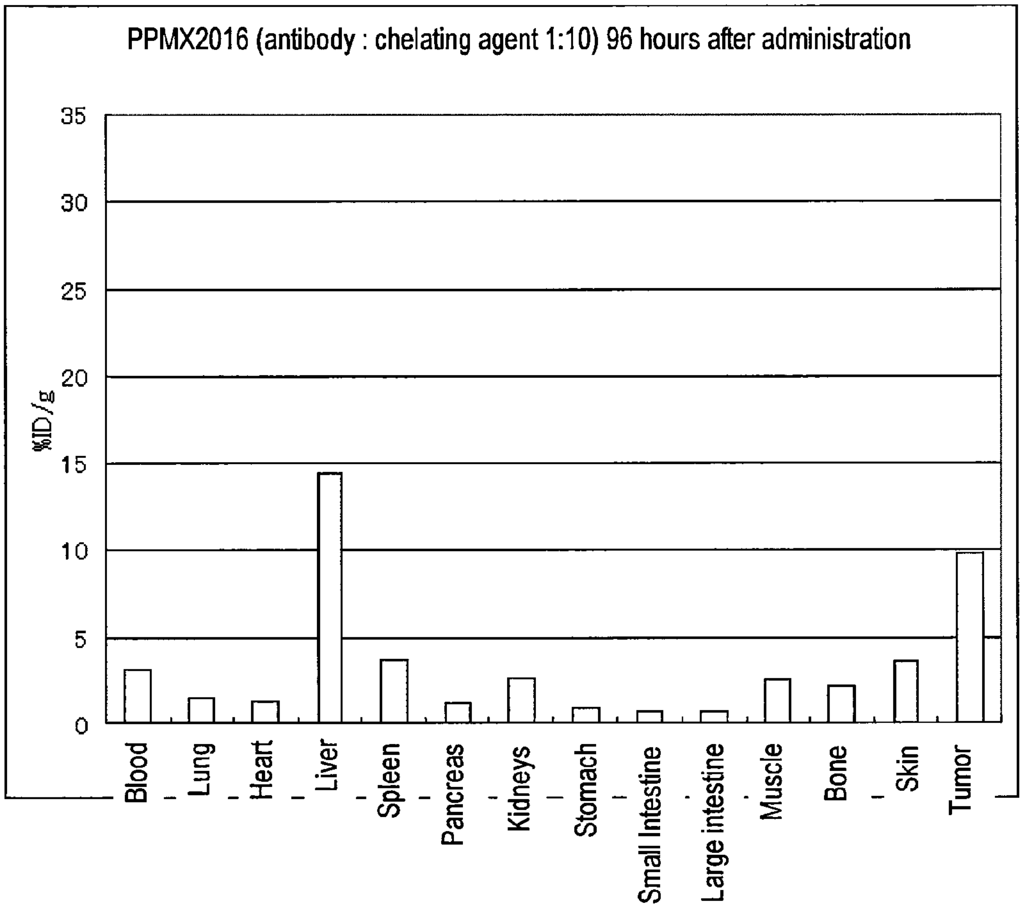
[FIG. 2] Bio-distribution of $^{67}$Ga-DOTA-PPMX2016 antibody (adding ratio of 1:10) 96 hours after administration thereof.
Figure 3:
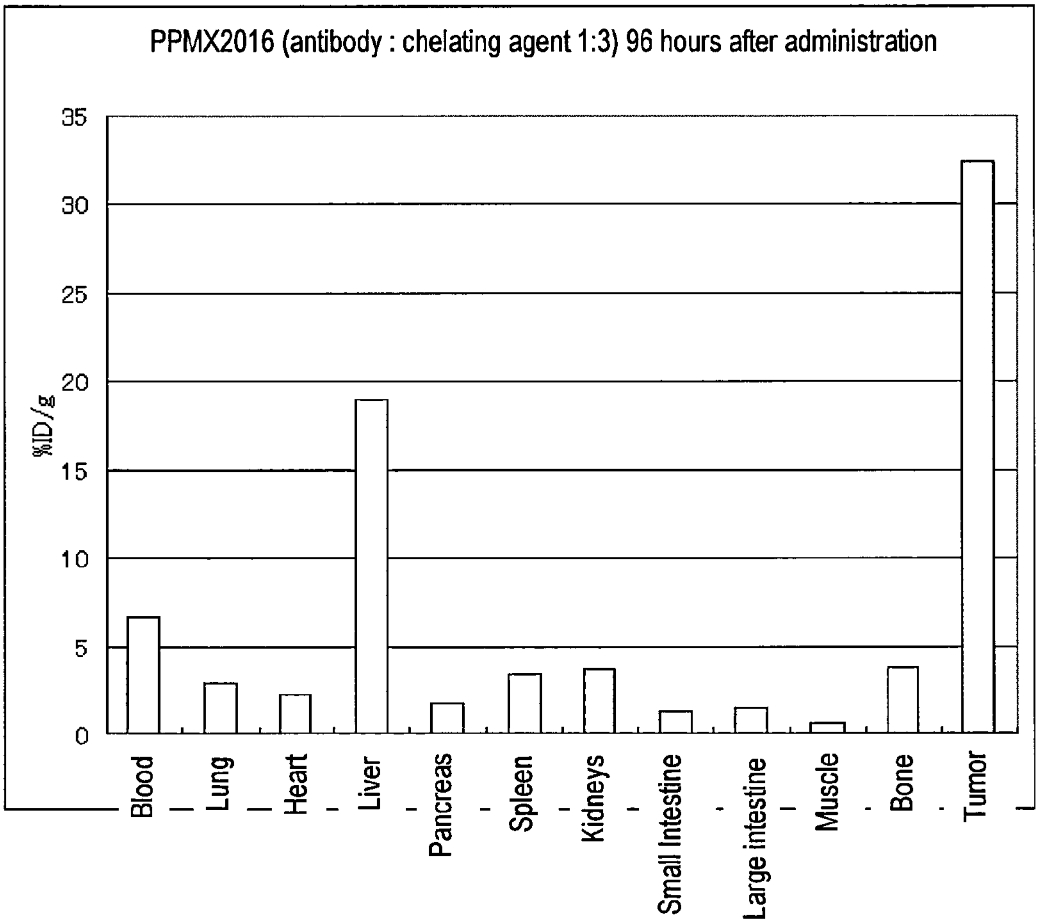
[FIG. 3] Bio-distribution of $^{67}$Ga-DOTA-PPMX2016 antibody (adding ratio of 1:3) 96 hours after administration thereof.
Figure 4:
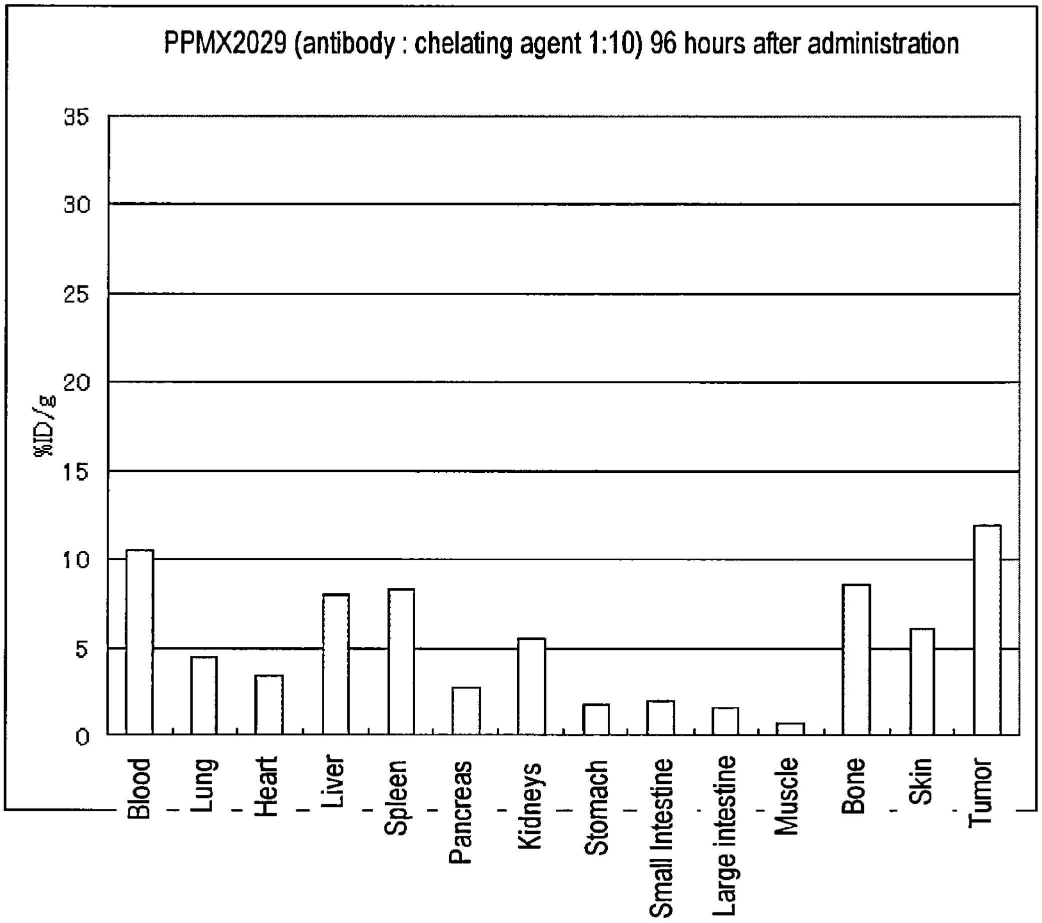
[FIG. 4] Bio-distribution of $^{67}$Ga-DOTA-PPMX2029 antibody (adding ratio of 1:10) 96 hours after administration thereof.
Figure 5:
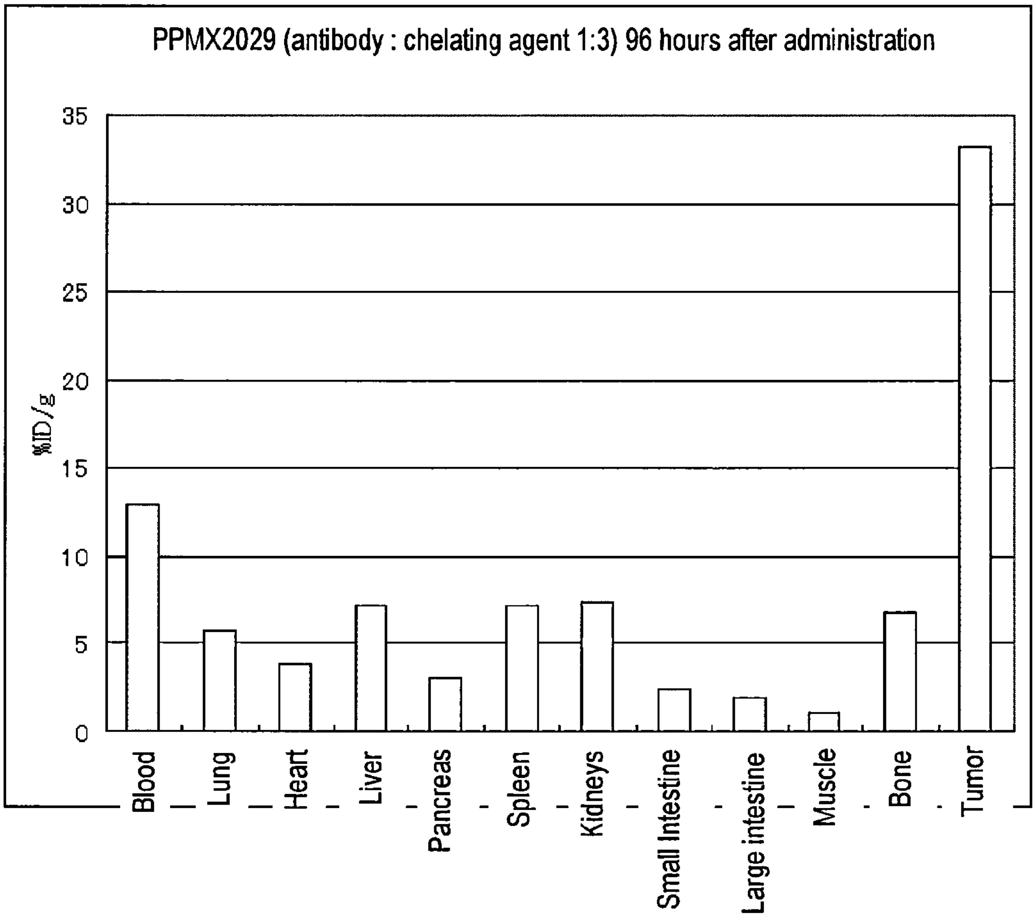
[FIG. 5] Bio-distribution of $^{67}$Ga-DOTA-PPMX2029 antibody (adding ratio of 1:3) 96 hours after administration thereof.
Figure 6:
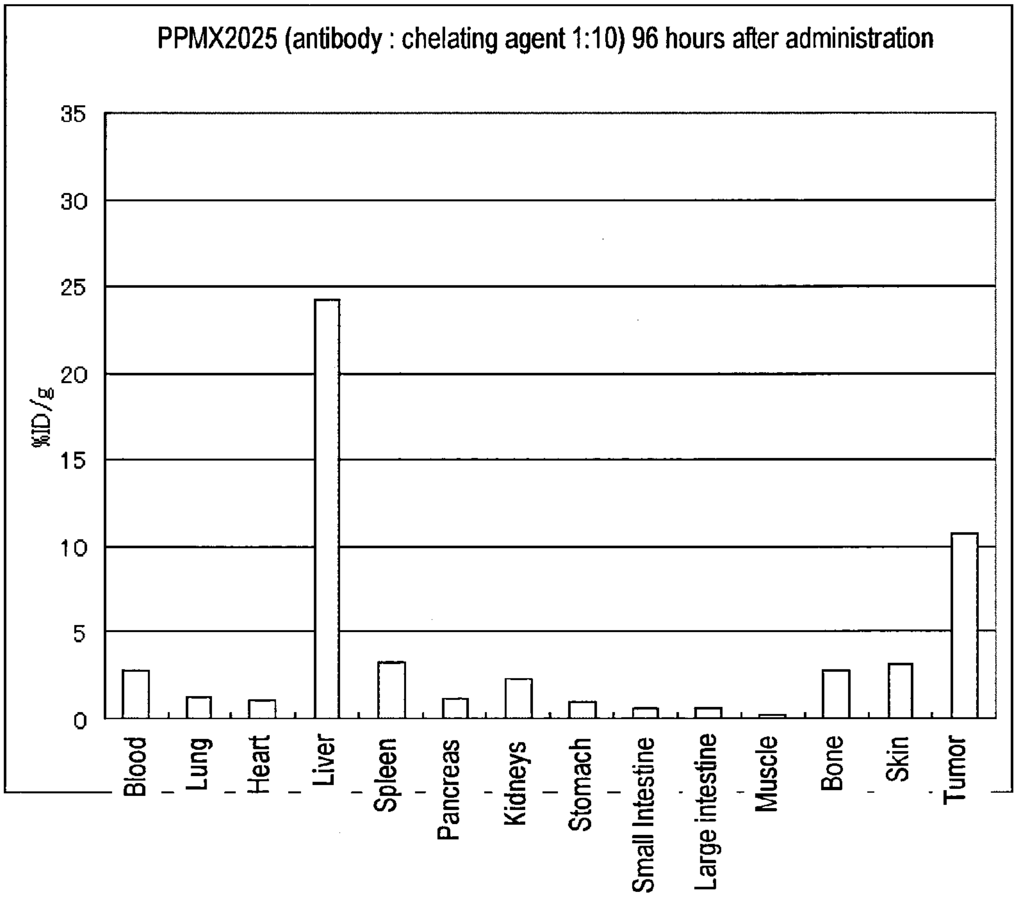
[FIG. 6] Bio-distribution of $^{67}$Ga-DOTA-PPMX2025 antibody (adding ratio of 1:10) 96 hours after administration thereof.
Figure 7:
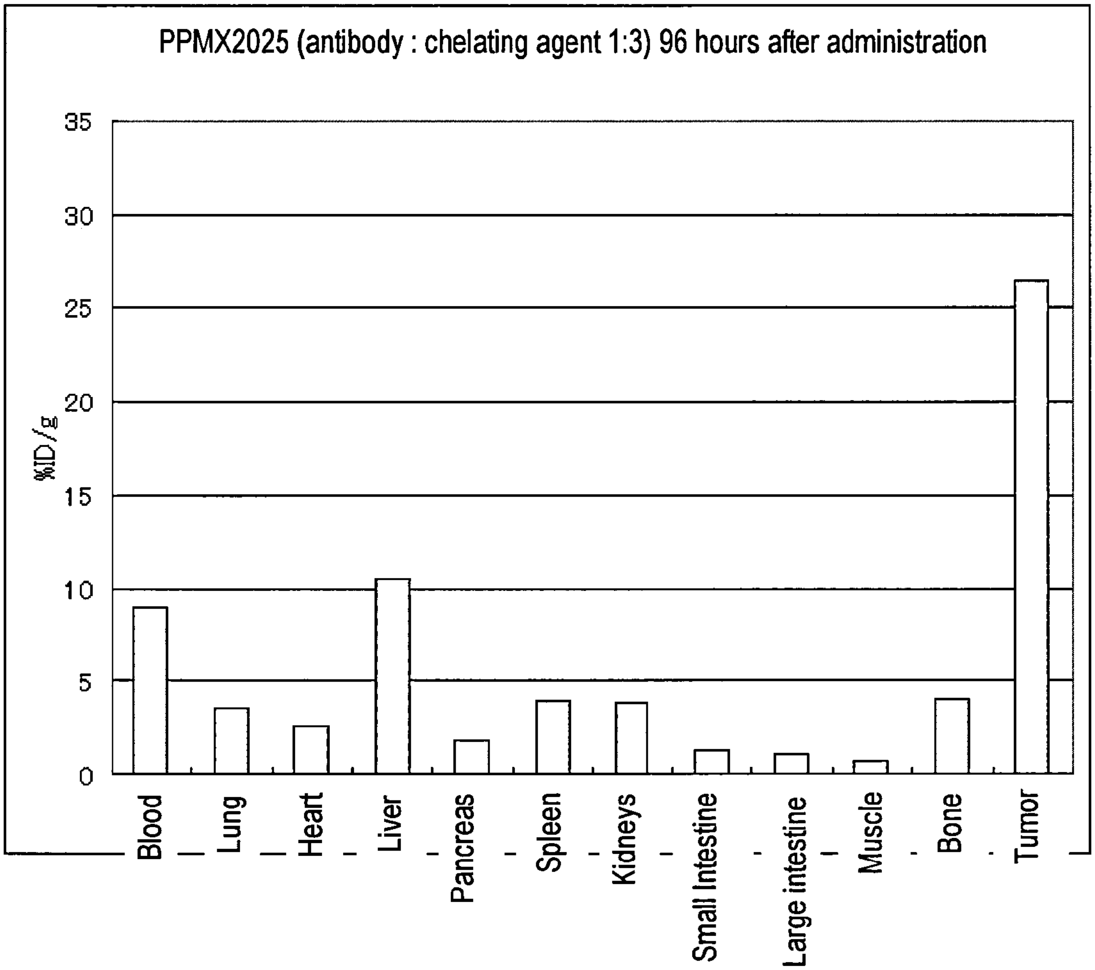
[FIG. 7] Bio-distribution of $^{67}$Ga-DOTA-PPMX2025 antibody (adding ratio of 1:3) 96 hours after administration thereof.

The radioactive metal-labeled anti-cadherin antibody of the present invention is a labeled anti-cadherin antibody to which a radioactive metallic element is bound to via a metal-chelating reagent. The cancer therapeutic agent or the cancer diagnostic agent contains the radioactive metal-labeled anti-cadherin antibody.

The anti-cadherin antibody is not particularly limited, so long as the antibody specifically binds to cadherin. Examples of cadherin include E cadherin, N cadherin, and P cadherin. Of these, P cadherin is more preferred.

The anti-cadherin antibody encompasses a monoclonal antibody, a polyclonal antibody, an antibody maintaining ability of binding specifically to an antigenic determinant group and variants and derivatives of an antibody such as T-cell receptor fragment.

The type of the anti-cadherin antibody is not particularly limited, and there may be appropriately employed antibodies such as a mouse antibody, a human antibody, a rat antibody, a rabbit antibody, a sheep antibody, a camel antibody, and a chicken antibody; and gene recombinant antibodies which are intentionally modified so as to reduce the hetero-antigenicity to human such as a chimeric antibody and a humanized antibody. The recombinant antibody may be produced through a known method. The chimeric antibody is an antibody formed of variable regions of a heavy chain and a light chain of a mammalian antibody other than human antibody, for example mouse antibody and constant regions of a heavy chain and a light chain of a human antibody and may be produced by linking a DNA fragment encoding the variable region of the mouse antibody to a DNA fragment encoding the constant region of the human antibody, incorporating the resultant fragment into an expression vector, and incorporating the vector into host cells (see, for example, Cabilly S. et al., Proc. Natl. Acad. Sci. USA, 1984, 81(11) 3273-7; Morrison et al., Proc. Natl. Acad. Sci. USA, 1984, 81(21), 6851-5; and European Patent Application Laid-Open No. 171496). The humanized antibody, which is also called a reshaped antibody, is an antibody produced through transplantation of a complementarity determining region (CDR) of a mammalian antibody other than human antibody, e.g., a mouse antibody into a CDR of a human antibody, and gene recombination techniques therefor are generally known. Specifically, a DNA sequence including a CDR of a mouse antibody linked to a framework region (FR) of a human antibody is synthesized through PCR using several oligonucleotides which are produced to have overlapped part at an end thereof. The thus-obtained DNA fragment is linked to a DNA fragment encoding the constant region of the human antibody, subsequently the resultant fragment is incorporated into an expression vector and the vector is incorporated into host cells to thereby produce the humanized antibody (see EP239400 A and WO 96/02576 A). The FR of the human antibody linked via the CDR is selected from FRs having a CDR which forms a suitable antigen-binding site. If needed, an amino acid in the FR of the variable region of the antibody may be substituted such that a CDR of the humanized antibody forms an appropriate antigen-binding site (Sato, K. et al., Cancer Res., 1993, 53, 851-856).

The amino acid sequence of the chimeric antibody or humanized antibody preferably has an identity of 100% to that of the VH or VL region of cDNA expressing a deposited hybridoma. Due to genetic modification, an antibody having an identity in amino acid sequence of 90% or higher is also preferred. In the process of humanization or chimerization, there has been conventionally carried out such controlled residue substitution for improving binding to an antigen. Such an antibody having a partially modified sequence is essentially considered to be an antibody originating from the original hybridoma.

Methods for producing a chimeric antibody and a humanized antibody based on a genetic engineering technique have been already known. Specifically, the VH and VL sequences of a monoclonal antibody serving as a confirmed group is genetically modified, and then chimerization or humanization is performed through a routine technique.

The method for recovering a human antibody is also known. In one procedure, human lymphocytes are sensitized in vitro with an antigen of interest or with cells expressing the antigen, and the thus-sensitized lymphocytes are fused with human myeloma cells, e.g., U266, to thereby produce a human antibody of interest having a binding activity to the antigen (see JP-B-1989-59878). Alternatively, a human antibody of interest may be recovered through immunization, with an antigen of interest, of a transgenic animal having a complete repertory of the human antibody gene (see WO 93/12227, WO 92/03918, WO 94/02602, WO 94/25585, WO96/34096, and WO96/33735). Also known is a technique for recovering a human antibody through panning by use of a human antibody library. In one procedure, a variable region of a human antibody is expressed as a single-chain antibody (scFv) on the phage surface through the phage display method, and a phage which binds the antigen can be selected. Through gene analysis of the thus-selected phage, a DNA sequence encoding the variable region of the human antibody which binds to the antigen can be determined. When the DNA sequence of the scFv which binds the antigen is elucidated, an appropriate expression vector can be produced from the sequence, whereby a human antibody of interest can be recovered. These methods are widely known (see WO 92/01047, WO 92/20791, WO 93/06213, WO 93/11236, WO 93/19172, WO 95/01438, and WO 95/15388).

These anti-cadherin antibodies may be a low molecule antibody such as an antibody fragment, a modified antibody or the like, so long as the ability of recognizing the entire or a part of the protein encoded by the cadherin gene is maintained. Examples of the antibody fragment include Fab, Fab', F(ab')2, Fv, and Diabody. Such an antibody fragment may be produced by constructing a gene encoding the antibody fragment, incorporating the gene into an expression vector, and expressing the vector in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

As a modified antibody, an antibody which is bound to any of various molecules such as polyethylene glycol (PEG) may be used. Such a modified antibody may be produced through chemical modification of the obtained antibody. The antibody modification technique has already been established in the art.

In the present invention, there may be also employed a sugar chain modified antibody for potentiating cytotoxic activity. Techniques of modifying the sugar chain in an antibody have already been known (e.g., WO 00/61739 and WO 02/31140).

The anti-cadherin antibody of the present invention also encompasses a multi-specific antibody having specificity to two or more different antigens. A typical example of such a molecule may be one which can bind two antigens (i.e., a bi-specific antibody). The "multi-specific antibody" of the present invention includes an antibody having a specificity to two or more (e.g., three) antigens. The multi-specific antibody may be a full-length antibody or a fragment of such an antibody (e.g., $F(ab')_2$ bi-specific antibody).

The anti-cadherin antibody of the present invention and the antibody fragment thereof may be produced through any suitable method such as in vivo, cultured cells, in vitro translation reaction, and recombinant DNA expression system.

Techniques of producing monoclonal antibodies and antibody-producing cells (hybridomas) are generally known in the art (Campbell, "Monoclonal Antibody Technology: Laboratory Techniques in Biochemistry and Molecular Biology," Elsevier Science Publishers, Amsterdam, The Netherlands, 1984; and St. Groth et al., J. Immunol. Methods 35: 1-21, 1980). In one specific procedure, a protein or a fragment thereof encoded by a cadherin gene serving as an immunogen is subcutaneously or intraperitoneally injected for immunization to any animal (e.g., mouse or rabbit) which is known to produce an antibody. In immunization, an adjuvant may be employed, and such an adjuvant is well known in the art.

The polyclonal antibody may be produced by isolating an anti-serum containing antibodies from an immunized animal and screening for the presence of an antibody having a target specificity through a technique well known in the art (e.g., ELISA, Western blotting, or radioimmunoassay).

The monoclonal antibody may be produced by removing spleen cells from an immunized animal and fusing the cells with myeloma cells, to thereby produce hybridomas which can produce monoclonal antibodies. Hybridoma cells producing an antibody which can recognize a protein of interest or a fragment thereof may be selected based on a technique well known in the art (e.g., ELISA, Western blotting, or radioimmunoassay). Then, the hybridoma secreting an antibody of interest is cloned, and the obtained cells are cultured under appropriate conditions. The thus-secreted antibody is recovered and purified through a method well known in the art (e.g., ion-exchange column chromatography or affinity chromatography). In an alternative procedure, a human monoclonal antibody may be produced by use of a xenomouse strain (see Green, J. Immunol. Methods 231: 11-23, 1999; and Wells, Eek, Chem. Biol. 2000 August; 7(8): R185-6). Currently, monoclonal antibody production based on phage display involving no immunization is carried out. The monoclonal antibody of the present invention is a single-molecular-species antibody produced by single-species of antibody-producing cells or a DNA fragment obtained therefrom and encoding the antibody. The monoclonal antibody may be produced through any of the aforementioned methods.

The DNA fragment encoding a monoclonal antibody can be readily isolated and sequenced through a routine method (e.g., by use of an oligonucleotide probe which can binds specifically to genes encoding the heavy chain and light chain of the monoclonal antibody). A hybridoma cell is a preferred starting material for producing such a DNA fragment. After isolation, such a DNA fragment is inserted into an expression vector, and the vector is recombined to host cells such as *E. coli* cells, monkey COS cells, Chinese hamster ovary (CHO) cells or myeloma cells in which no immunoglobulin is produced unless the cells are transformed. The monoclonal antibody of interest is produced by the recombinant host cells. In an alternative mode, an antibody or an antibody fragment can be isolated from an antibody phage library produced through a technique of McCafferty et al. (Nature 348: 552-554 (1990)).

The host cell employed for monoclonal antibody expression is preferably a mammal-origin host cell. A host cell most suited to a monoclonal antibody to be expressed may be selected. The host cell is not limited and typical examples thereof include CHO-originating cell line (Chinese hamster ovary cell), CV1 (monkey kidney), COS (CV1 derivative expressing SV4OT antigen), SP2/0 (mouse myeloma), P3x63-Ag3.653 (mouse myeloma), 293 (human kidney), and 293T (293 derivative expressing SV4OT antigen). The host cell system may be obtained from a commercial facility, the American Tissue Culture Collection (ATCC), or an organization which published a relevant document.

The host cell is preferably a dhfr gene expression-defective CHO-originating cell line (deletion in dhfr gene expression) or SP2/0 (see Urland, G. et al., Effect of gamma rays at the dihydrofolate reductase locus: deletions and inversions; Somat. Cell. Mol. Genet. Vol. 12, 1986, p. 5555-566; and Schulman, M. et al., A better cell line for making hybridomas secreting specific antibodies, Nature Vol. 276, 1978, p. 269-270). The host cell is more preferably a DHFR-deleted CHO. Transfection of a plasmid into host cells may be performed through any technique. Transfection technique is not limited and specific examples thereof include transfection (including calcium phosphate method, DEAE method, lipofection, and electroporation), DNA incorporation by use of an envelope (e.g., Sendai virus), micro-injection, and infection by use of a viral (e.g., retrovirus or adenovirus) vector (see Current Protocols in Molecular Biology, Chapter 9 Introduction of DNA into Mammalian Cells, John Wiley and Sons, Inc.). Among them, incorporation of a plasmid into host cells through electroporation is particularly preferred.

The recognition site in cadherin of the anti-cadherin antibody of the present invention is preferably a region from 1 to 655 of SEQ ID NO: 2.

The anti-cadherin antibody of the present invention is preferably produced from a hybridoma PPMX2016, PPMX2025, PPMX2029, PPAT-052-02, PPAT-052-03, PPAT-052-09, PPAT-052-24, PPAT-052-25, PPAT-052-26, or PPAT-052-28, or an transgenic CHO cell line PPAT-052-27c, PPAT-052-02c, PPAT-052-03c, PPAT-052-09c, PPAT-052-21c, PPAT-052-24c, PPAT-052-25c, PPAT-052-26c, PPAT-052-28c, or PPAT-052-29c. In the present specification, the numbers attached to PPMX or PPAT are given to either corresponding antibody-producing cells or antibodies produced by the antibody-producing cells.

A radioactive metal which is bound to the anti-cadherin antibody is preferably a cytotoxic radioactive metal when the radioactive metal-labeled anti-cadherin antibody is used as a cancer therapeutic agent, and a non-cytotoxic radioactive metal when the radioactive metal-labeled anti-cadherin antibody is used as a cancer diagnostic agent.

Examples of the cytotoxic radioactive metal include yttrium-90 ($^{90}Y$), rhenium-186 ($^{186}Re$), rhenium-188 ($^{188}Re$), copper-67 ($^{67}Cu$), iron-59 ($^{59}Fe$), strontium-89 ($^{89}Sr$), gold-198 ($^{198}Au$), mercury-203 ($^{203}Hg$), lead-212 ($^{212}Pb$), dysprosium-165 ($^{165}Dy$), ruthenium-103 ($^{103}Ru$), bismuth-212 ($^{212}Bi$), bismuth-213 ($^{213}Bi$), holmium-166 ($^{166}Ho$), samarium-153 ($^{153}Sm$), and lutetium-177 ($^{177}Lu$).

Among these radioactive metals, $^{90}Y$, $^{153}Sm$, and $^{177}Lu$ are preferred, from the viewpoints of half-life, radiation energy, ease of labeling reaction, percent of labeling, complex stability, etc.

A non-cytotoxic radioactive metal suitably employed in a cancer diagnostic agent is not limited and examples thereof include technetium-99m ($^{99m}Tc$), indium-111 ($^{111}In$), indium-113m ($^{113m}In$), gallium-67 ($^{67}Ga$), gallium-68 ($^{68}Ga$), thallium-201 ($^{201}Tl$), chromium-51 ($^{51}Cr$), cobalt-57 ($^{57}Co$), cobalt-58 ($^{58}Co$), cobalt-60 ($^{60}Co$), strontium-85 ($^{85}Sr$), mercury-197 ($^{197}Hg$), and copper-64 ($^{64}Cu$).

For bonding a radioactive metallic element to the anti-cadherin antibody, in a preferred mode, a metal-chelating reagent is reacted with the anti-cadherin antibody, and the product is further reacted with a radioactive metallic element, to thereby form a complex. In the thus-produced modified antibody, the radioactive metallic element is bound to the anti-cadherin antibody via the metal-chelating reagent.

Examples of the metal-chelating reagent for forming such a complex include (1) quinoline derivatives such as 8-hydroxyquinoline, 8-acetoxyquinoline, 8-hydroxyquinaldine, oxyquinoline sulfate, O-acetyloxine, O-benzoyloxine, O-p-nitrobenzoyloxine, and quinolone compounds having a quinoline skeleton (e.g., norfloxacin, ofloxacin, enoxacin, ciprofloxacin, lomefloxacin, tosfloxacin, fleroxacin, and sparfloxacin); (2) compounds such as chloranilic acid, aluminon, thiourea, pyrogallol, cupferron, Bismuthiol (II), galloyl gallic acid, thiolide, 2-mercaptobenzothiazole, and tetraphenylarsonium chloride; (3) ethylenediaminetetraacetic acid (EDTA), diethylenetriaminepentaacetic acid (DTPA), and compounds having a similar skeleton (dihydroxyethylglycine, diaminopropanolte traacetic acid, ethylenediamine diacetic acid, ethylenediaminedipropionic acid hydrochloride, hydroxyethylethylenediaminetriacetic acid, ethylenediaminetetrakis(methylenesulfonic acid), glycol ether diaminetetraacetic acid, hexamethylenediaminetetraacetic acid, hydroxyethyliminodiacetic acid, iminodiacetic acid, diaminopropanetetraacetic acid, nitrilotriacetic acid, nitrilotripropionic acid, nitrilotris(methylenesulfonic acid) trisodium salt, triethylenetetraminehexaacetic acid, methyl DTPA, cyclohexyl DTPA, aminobenzyl EDTA, isothiocyanobenzyl EDTA, isothiocyanobenzyl DTPA, methylisothiocyanobenzyl DTPA, cyclohexylisothiocyanobenzyl DTPA, maleimidopropylamidobenzyl EDTA, maleimidopentylamidobenzyl EDTA, maleimidodecylamidobenzyl EDTA, maleimidopentylamidobenzyl DTPA, and maleimidodecylamidobenzyl DTPA); and (4)1,4,7,10-tetraazacyclododecane-1,4,7,10-tetraacetic acid (DOTA), 1,4,7-triazacyclononane-1,4,7-triacetic acid (NOTA), 1,4,8,11-tetraazacyclotetradecane-1,4,8,11-tetraacetic acid (TETA), 1,4,7,10-tetraazacyclododecane (Cyclen), 1,4,8,11-tetraazacyclotetradecan (Cyclam), isothiocyanobenzyl DOTA, and isothiocyanobenzyl NOTA.

Among these metal-chelating reagents, isothiocyanobenzyl DOTA, methylisothiocyanobenzyl DTPA, cyclohexylisothiocyanobenzyl DTPA are preferred, from the viewpoints of ease of incorporation reaction of metal-chelate to antibody, percent of labeling, complex stability, etc.

The radioactive metallic element may be bound to the anti-cadherin antibody through a routine method. In one procedure, a metal-chelating reagent is reacted with an anti-cadherin antibody, to thereby prepare a label precursor, and the precursor is reacted with a radioactive metallic element.

In the cancer therapeutic agent and cancer diagnostic agent of the present invention, the ratio by mole of anti-cadherin antibody to metal-chelating reagent is important for accumulation in cancer cells and anti-cancer effect. The mole ratio (anti-cadherin antibody : chelating reagent) is preferably 1:0.1 to 1:4.5, more preferably 1:0.5 to 1:3. In order to attain such mole ratios, the anti-cadherin antibody and the chelating reagent are preferably added to react at a ratio of 1:0.1 to 1:less than 5, particularly preferably 1:1 to 1:3. The number of chelate molecule(s) per anti-cadherin antibody may be calculated by measuring molecular weight through MALDI-TOF mass analysis or a similar technique, and comparing the molecular weight of an unmodified antibody to that of a modified antibody (U.S. Patent Publication No. 7514078, Lu et al., J. Pharm. Sci. 94(4), 2005, p. 788-797, and Tedesco et al., J. Clin. Onco. 23 (16S), 2005, 4765). Alternatively, the number of chelate molecule(s) per anti-cadherin antibody may be determined through chelatometric titration. One known method employs an alkaline earth metal calorimetric reagent (arsenazo III) (Bradyr et al., Nucl. Med. Biol. 31, 795-802, 2004, and Dadachova et al., Nucl. Med. Biol. 26, 977-982, 1999).

The cancer therapeutic agent or cancer diagnostic agent of the present invention may be provided as a labeled formulation or a kit formulation containing a label precursor. Either formulation may be employed in the present invention. In the case of labeled formulation, a cancer therapeutic agent or a cancer diagnostic agent containing a labeled anti-cadherin antibody may be administered as is. In the case of a kit formulation, the agent may be administered after labeling with a radioactive metallic element of interest.

The anti-cadherin antibody containing a radioactive metallic element bound thereto highly accumulates in cancer tissue and exhibits high cancer cell-toxic activity. Thus, the antibody is a useful cancer therapeutic agent which less damages the tissue other than cancer tissue and which has high safety. Also, the anti-cadherin antibody containing a radioactive metallic element bound thereto has an anti-cancer activity remarkably higher than that of a corresponding anti-cadherin antibody. The anti-cancer activity is remarkably high particularly when the mole ratio of antibody to chelating agent is 1:0.1 to 1:4.5.

The cancer therapeutic agent of the present invention may be used in combination with another anti-cancer agent. Examples of such an anti-cancer agent include an alkylating agent, an antimetabolite, a microtubule inhibitor, an antibiotic anti-cancer agent, a topoisomerase inhibitor, a platinum agent, a molecular target drug, a hormone agent, and a biologics. Examples of the alkylating agent include nitrogen mustard anti-cancer agents (e.g., cyclophosphamide), nitrosourea anti-cancer agents (e.g., ranimustine), and dacarbazine. Examples of the antimetabolite include 5-FU, UFT, carmofur, capecitabine, tegafur, TS-1, gemcitabine, and cytarabine. Examples of the microtubule inhibitor include alkaloid anti-cancer agents (e.g., vincristine) and taxane anti-cancer agents (e.g., docetaxel and paclitaxel). Examples of the antibiotic anti-cancer agent include mitomycin C, doxorubicin, epirubicin, daunorubicin, and bleomycine. Examples of the topoisomerase inhibitor include irinotecan and nogitecan having topoisomerase I inhibiting activity and etoposide having topoisomerase II inhibiting activity. Examples of the platinum agent include cisplatin, paraplatin, nedaplatin, and oxaliplatin. Examples of the molecular target drug include trastuzumab, rituximab, imatinib, gefitinib, erlotinib, bevacizumab, bortezomib, sunitinib, and sorafenib. Examples of the hormone agent include dexamethasone, finasteride, and tamoxifen. Examples of the biologics include interferons α, β and γ and interleukin 2.

The cancer therapeutic agent of the present invention may be used in combination with a cancer therapy. Examples of the cancer therapy include surgery, radiation therapies (including gamma knife therapy, Cyber knife therapy, boron neutron capture therapy, and proton beam/heavy ion beam therapy), MR-guided focused ultrasound surgery, cryotherapy, radiofrequency ablation, percutaneous ethanol injection therapy, and embolotherapy.

The cancer therapeutic agent of the present invention is effective on various cancers of a mammal (including a human). Examples of the target cancer include carcinomas such as pharyngeal cancer, laryngeal cancer, tongue cancer, lung cancer, breast cancer, esophageal cancer, stomach cancer, colorectal cancer, uterine cancer, ovarian cancer, liver cancer, pancreatic cancer, gallbladder cancer, kidney cancer, prostatic cancer, malignant melanoma, and thyroid cancer; and sarcomas such as osteosarcoma, chondrosarcoma, rhabdomyosarcoma, leiomyosarcome, liposarcoma, angiosarcoma, fibrosarcoma, leukemia, malignant lymphoma, and myeloma.

The cancer therapeutic agent of the present invention may be dissolved in an aqueous solution, preferably a physiologically adaptable buffer such as Hanks' solution, Ringer's solution, or buffered physiological saline. Also, the therapeutic agent may have the form of suspension, solution, emulsion, or the like in an oily or aqueous vehicle.

The dosage of the cancer therapeutic agent of the present invention, which varies in accordance with the symptom, administration route, body weight, age, etc. of a patient in need thereof, is preferably, for example, 37 to 3,700 MBq for one treatment of adult.

The cancer therapeutic agent of the present invention is generally administered parenterally. For example, the cancer therapeutic agent is injected (e.g., subcutaneously, intravenous, intramuscle, intraperitoneally) or administered transdermally, transmucosally, transnasally, transplumonarily, etc.

The cancer diagnostic agent of the present invention may be used in tumor imaging. In the case where a patient has a tumor in which CDH3 protein is expressed, the cancer diagnostic agent of the present invention accumulates in the tumor. Thus, the tumor can be imaged by detecting radiation by means of an apparatus such as a single photon emission computed tomograph (SPECT), a positron emission tomograph (PET), or a scintillation camera. For example, by use of the cancer diagnostic agent of the present invention, the therapeutic effect of the cancer therapeutic agent of the present invention can be predicted before administration of the therapeutic agent. The diagnostic agent is administered to a patient before the treatment, and the tumor is imaged. When high accumulation is observed, the superior effect of the therapeutic agent can be predicted as potent. The diagnostic agent may be used for determining the therapeutic effect. The diagnostic agent of the present invention is administered to a patient who has received the treatment with the therapeutic agent of the present invention or any other treatment so as to image the tumor. Through monitoring the time-dependent variation in accumulation of the diagnostic agent, the expansion or shrinkage of the tumor over time can be observed.

The antibody for use as a diagnostic agent preferably recognizes an epitope competitive to a therapeutic agent. More preferably, the antibody recognizes the same epitope as that recognized by the therapeutic agent. Most preferably, the therapeutic agent and the diagnostic agent are the same antibody.

The cancer diagnostic agent of the present invention is generally administered to a subject intravenously. However, the cancer diagnostic agent may also be administered arterially. The dosage thereof, which varies in accordance with the symptom, administration route, body weight, age, etc. of a patient in need thereof, is preferably, for example, 37 to 1,120 MBq for one treatment of adult.

EXAMPLES

The present invention will next be described in detail by way of examples, which should not be construed as limiting the invention thereto.

Example 1

Production of Soluble CDH3 Antigen

Soluble CDH3 (sCDH3) protein in which the C-terminal transmembrane region had been deleted was produced to serve as an immunogen for producing an anti-CDH3 antibody.

(1) Production of soluble CDH3 antigen expression vector

PCR was performed by use of a CDH3 full-length cDNA as a template and a forward primer (SEQ ID NO: 3: CGCGGTACCATGGGGCTCCCTCGT, (hCDH3Full FW)) and a reverse primer (SEQ ID NO: 4: CCGTCTAGATAACCTCCCTTCCAGGGTCC, (hCDH3SolbRV)), which had been designed so as to amplify a segment corresponding to the CDH3 extracellular region (1-654 in SEQ ID NO: 2, hereinafter referred to as sCDH3cDNA). The reaction was performed by use of KOD-Plus (product of Toyobo) and under the following conditions: 94° C.-15 sec, 55° C.-30 sec, and 68° C.-90 sec (30 cycles)).

After completion of the PCR reaction, the reaction mixture was subjected to agarose gel electrophoresis, and a gel piece containing a band of a target size (about 2.0 kbp) was cut out. The target sCDH3cDNA was recovered from the gel piece by use of a QIA quick gel extraction kit (product of Quiagen).

In order to insert sCDH3cDNA into an expression vector pEF4/myc-HisB, sCDH3cDNA was treated with two restriction enzymes KpnI and XbaI. The thus-obtained fragment was inserted into pEF4/myc-HisB which had been treated with the same restriction enzymes KpnI and XbaI, by use of T4 DNA ligase through a routine technique, whereby an expression vector pEF4-sCDH3-myc-His was yielded.

(2) Expression of soluble CDH3 protein

According to a protocol of an FuGENE6 transfection reagent, $8\times10^5$ CHO cells were inoculated to a 10-cm-diameter dish on the day before transfection, and the cells were cultured overnight. Thereafter, an expression vector pEF4-sCDH3-myc-His (8 μg) and an FuGENE6 regent (16 μL) were mixed with serum-free RPMI 1640 medium (400 μL), and the mixture was allowed to stand at room temperature for 15 minutes. The resultant mixture was added to the cell culture liquid for transfection. Two days after transfection, cloning was performed through limiting dilution by use of a selection reagent (Zeocin).

Soluble CDH3-expressing CHO cells were selected through Western blotting by use of an anti-c-Myc monoclonal antibody (product of SANTA CRUZ BIOTECHNOLOGY).

Cell lines which exhibited high level of secretion into the culture supernatant and high proliferation were selected to obtain a soluble CDH3-expressing CHO cell line (EXZ1702). The thus-selected soluble CDH3-expressing CHO cells (EXZ1702) were cultured for 72 hours in three roller bottles (each culture area: 1,500 $cm^2$) with serum-free medium CHO-S-SFM-II (333 mL/bottle) (product of Invitrogen), and the culture supernatants were recovered. The thus-obtained culture supernatant was subjected to affinity chromatography by means of HisTrap (registered trademark) HP column (product of GE Healthcare Bio-science) and gel filtration chromatography by means of Superdex (registered trademark) 200 pg column (product of GE Healthcare Bio-science), to thereby acquire soluble CDH3 protein.

Example 2

Establishment of CDH3-expressing CHO Cell Line

For obtaining a cell line for anti-CDH3 antibody screening, a CHO cell line expressing full length CDH3 was established.

(1) Production of CDH3 gene expression vector

In order to insert full-length human CDH3 DNA represented by SEQ ID NO: 1 into a mammal expression vector pEF4/myc-HisB (product of Invitrogen), the full-length human CDH3 DNA was treated with two restriction enzymes KpnI (product of Takara Bio Inc.) and XbaI (product of Takara Bio Inc.) at 37° C. for one hour. The thus-obtained fragment was inserted into pEF4/myc-HisB which had been treated with the same restriction enzymes KpnI and XbaI, by use of T4 DNA ligase (product of Promega) through a routine technique, whereby an expression vector pEF4-CDH3-myc-His was produced.

(2) Acquisition of stable CDH3-expressing line

According to a protocol of an FuGENE (registered trademark) 6 transfection reagent (product of Roche Diagnostics K.K.), $8\times10^5$ CHO cells were inoculated to a 10-cm-diameter dish on the day before transfection, and the cells were cultured overnight. Thereafter, an expression vector pEF4-CDH3-myc-His (8 μg) and an FuGENE6 regent (16 μL) were mixed with serum-free RPMI 1640 medium (product of SIGMA-ALDRICH) (400 μL), and the mixture was allowed to stand at room temperature for 15 minutes. The resultant mixture was added to the cell culture liquid for transfection. Two days after transfection, cloning was performed through limiting dilution by use of a selection reagent (Zeocin).

Clones of CDH3 full-length expressing CHO were selected through Western blotting by use of an anti-c-Myc monoclonal antibody (product of SANTA CRUZ BIOTECHNOLOGY). As a result, a CDH3 full-length expressing CHO cell line (EXZ1501) was selected as a cell line which exhibited high level of expression and high proliferation. The reaction between EXZ1501 and a commercial anti-CDH3 antibody (product of R&D SYSTEMS) was confirmed through flow cytometry. That is, CDH3 protein expression on the cell membrane of EXZ1501 was confirmed.

Example 3

Production of Anti-CDH3 Monoclonal Antibody (1) Production of monoclonal antibody by use of soluble CDH3 protein as an immunogen Soluble CDH3 protein (50 μg) dissolved in physiological saline was mixed with an equal amount of Titer-MAX Gold (registered trademark) (product of Titer Max), and the mixture was intraperitoneally and subcutaneously injected to MRL/lpr mice (Japan SLC inc.) for initial immunization. Subsequent immunization procedures were performed by intraperitoneally and subcutaneously injecting, to the mice, a mixture of soluble CDH3 protein (25 μg) and Titer-MAX Gold prepared in the same manner. Three days after final immunization, spleen cells were prepared from the mice under aseptic conditions, and the cells were fused with mouse myeloma cells SP2/O-Ag14 or P3-X63-Ag8.653 through a generally employed polyethylene glycol method.

(2) Selection of anti-CDH3 antibody-producing hybridomas

Selection of anti-CDH3 antibodies were performed through flow cytometry by use of a full-length CDH3-expressing CHO cell line (EXZ1501).

Specifically, full-length CDH3-expressing CHO cells (EXZ1501) were removed from a culture plate by treating with 2 mM EDTA-PBS and suspended in FACS solution to a cell concentration of $1\times10^6$ cells/mL. The cell suspension was inoculated to a 96-well plate to a concentration of 50 μL/well, and a hybridoma culture supernatant was added thereto, followed by reaction at 4° C. for 60 minutes. The plate was washed twice with FACS solution (200 μL/well), and Alexa Fluor 488-labeled anti-mouse IgG·goat F(ab')2 (product of Invitrogen) was added thereto, followed by reaction at 4° C. for 30 minutes. Subsequently, the plate was washed twice with FACS solution, and flow cytometry was performed, to thereby select hybridomas producing an antibody which binds to CDH3-expressing CHO cells. As a result, 40 clones PPMX2016 to PPAT-052-28 were obtained. Through flow cytometry, it was confirmed that all the hybridomas reacted with CDH3-expressing CHO cells (EXZ1501) and NCI-H358 but do not react with CHO cells. Antibodies were purified from the hybridoma culture supernatant by means of Protein G column and employed in the subsequent experiments. Among the selected hybridomas, PPMX2016 (NITE BP-897), PPMX2025 (NITE BP-898), PPMX2029 (NITE BP-899), PPAT-052-02 (NITE BP-1034), PPAT-052-03 (NITE BP-1035), PPAT-052-09 (NITE BP-1036), PPAT-052-24 (NITE BP-1037), PPAT-052-25 (NITE BP-1038), PPAT-052-26 (NITE BP-1039), and PPAT-052-28(NITE BP-1040) were deposited with Incorporated Administrative Agency, the National Institute of Technology and Evaluation, Patent Microorganisms Depositary (2-5-8, Kazusakamatari, Kisarazu-shi, Chiba, Japan) on Feb. 10, 2010 and Jan. 18, 2011.

Example 4

Cloning of Antibody Genes (1) A DNA fragment encoding the V-region of a mouse monoclonal antibody to human CDH3 was cloned through the following procedure. Cytoplasmic RNA was isolated from the mouse hybridoma cells through a method disclosed in a document (Gough, “Rapid and quantitative preparation of cytoplasmic RNA from small numbers of cells,” Analytical Biochemisty, 173, p. 93-95 (1988)), with the proviso that instead of the dissolution buffer disclosed in the document, a TNE buffer (i.e., 25 mM Tris-HCl, pH: 7.5; 1% NP-40; 150 mM NaCl; 1 mM EDTA, pH: 8.0)was employed. More specifically, $5\times10^6$ hybridoma cells were suspended in the TNE buffer (200 μL), to thereby dissolve cell membranes, and cell nuclei were removed through centrifugation. To the thus-obtained cytoplasma supernatant (about 200 μL), an extraction buffer (10 mM Tris-HCl, pH: 7.5; 0.35M NaCl; 1% (w/v) SDS; 10 mM EDTA, pH: 8.0; 7M urea) (200 μL) was added. The mixture was subjected to extraction with phenol and chloroform. To the thus-obtained RNA solution, glycogen (product of Roche, Cat No. 901393) serving as a carrier was added. Then, ethanol was added to precipitate the product. The RNA precipitate was dissolved in sterilized distilled water (10 to 50 μL) to a cytoplasmic RNA concentration of 0.5 to 2 μg/μL.

(2) Production of cDNA Library from RNA Prepared from Hybridomas

For synthesizing a single-strand cDNA, there was prepared a reaction mixture (20 μL) containing the above-prepared cytoplasmic RNA (0.5 to 3 μg), 50 mM Tris-HCl (pH: 8.3, room temperature), 75 mM KCl, 3 mM $MgCl_2$, and 10 mM DTT), a random primer (100 ng), 0.5 mM dNTP, and Superscript II (reverse transcriptase, product of Invitrogen) (200 units). The mixture was incubated at 42° C. for 50 minutes. The thus-synthesized cDNA library was employed as a template of polymerase chain reaction (PCR) without performing further treatment.

(3) Amplification of a Gene Encoding a Variable Region of Anti-CDH3 Antibody Through PCR All the primers employed in the experiments were synthesized by Hokkaido System Science Co., Ltd.

A. Primers for use in PCR Amplification of a Gene Encoding Mouse L-chain V-region The following two primer sets were employed: (i) a DNA primer having, at the 5' end, a homology to the FR1 part and 4-set primers having, at the 3' end, a homology to a J-chain gene in the mouse L-chain, and (ii) 7-set primers having, at the 5' end, a homology to the L-chain signal part and an antisense primer having, at the 3' end, a homology to the KC part (KVL antisense primer). Polymerase chain reaction was performed by use of the two primer sets, whereby a mouse immunoglobulin L-chain variable region DNA fragment was obtained from the cDNA. The primer sequences are as follows.

(i) 4-Set Sense Primers for Mouse L-chain Variable Region Cloning

According to "Phage Display—A Laboratory Manual—, Barbas Burton Scott Silverman," PROTOCOL 9.5, 17 sense primers and 3 reverse primers were synthesized by Hokkaido System Science Co., Ltd.

VK Sense (FR1 part)

A mixture of the following 17 primers was employed as a VK sense primer.

```
SEQ ID NO: 5
5'-GAY ATC CAG CTG ACT CAG CC-3' (degeneracy 2):

SEQ ID NO: 6
5'-GAY ATT GTT CTC WCC CAG TC-3' (degeneracy 4):

SEQ ID NO: 7
5'-GAY ATT GTG MTM ACT CAG TC-3' (degeneracy 8):

SEQ ID NO: 8
5' GAY ATT GTG YTR ACA CAG TC-3' (degeneracy 8):

SEQ ID NO: 9
5' GAY ATT GTR ATG ACM CAG TC-3' (degeneracy 8):

SEQ ID NO: 10
5' GAY ATT MAG ATR AMC CAG TC-3' (degeneracy 16):

SEQ ID NO: 11
5' GAY ATT CAG ATG AYD CAG TC-3' (degeneracy 12):

SEQ ID NO: 12
5' GAY ATY CAG ATG ACA CAG AC-3' (degeneracy 4):

SEQ ID NO: 13
5' GAY ATT GTT CTC AWC CAG TC-3' (degeneracy 4):
```

-continued

```
SEQ ID NO: 14
5' GAY ATT GWG CTS ACC CAA TC-3' (degeneracy 8):

SEQ ID NO: 15
5' GAY ATT STR ATG ACC CAR TC-3' (degeneracy 16):

SEQ ID NO: 16
5' GAY RTT KTG ATG ACC CAR AC-3' (degeneracy 16):

SEQ ID NO: 17
5' GAY ATT GTG ATG ACB CAG KC-3' (degeneracy 12):

SEQ ID NO: 18
5' GAY ATT GTG ATA ACY CAG GA-3' (degeneracy 4):

SEQ ID NO: 19
5' GAY ATT GTG ATG ACC CAG WT-3' (degeneracy 4):

SEQ ID NO: 20
5' GAY ATT GTG ATG ACA CAA CC-3' (degeneracy 2):

SEQ ID NO: 21
5' GAY ATT TTG CTG ACT CAG TC-3' (degeneracy 2):
```

J Antisense (4-set Primers)

J1/J2 Antisense Primer (1)

```
SEQ ID NO: 22
5'-GGS ACC AAR CTG GAA ATM AAA-3' (degeneracy 8):
```

J4 Antisense Primer (2)

```
SEQ ID NO: 23
1'-GGG ACA AAG TTG GAA ATA AAA-3':
```

J5 Antisense Primer (3)

```
SEQ ID NO: 24
1'-GGG ACC AAG CTG GAG CTG AAA-3':
```

J1/J2, J4, J5 Antisense Primer Mixture (4)

(ii) 7-Set Primers for Mouse L-chain Variable Region Cloning VK Sense (Signal Peptide Part)

The primers were obtained through nucleotide sequence modification of a mouse Ig-primer set (Novagen; Merck, Cat. No. 69831-3) such that restriction enzyme sites were removed.

A-set Sense Primer

```
SEQ ID NO: 25
1'-ATGRAGWCACAKWCYCAGGTCTTT-3':
```

B-set Sense Primer

```
SEQ ID NO: 26
1'-ATGGAGACAGACACACTCCTGCTAT-3':
```

C-set Sense Primer

```
SEQ ID NO: 27
1'-ATGGAGWCAGACACACTSCTGYTATGGGT-3':
```

D-set Sense Primer (Mixture of the Following 2 Primers)

SEQ ID NO: 28
1'-ATGAGGRCCCCTGCTCAGWTTYTTGGIWTCTT-3':

SEQ ID NO: 29
1'-ATGGGCWTCAAGATGRAGTCACAKWYYCWGG-3':

E-set Sense Primer (Mixture of the Following 3 Primers)

SEQ ID NO: 30
1'-ATGAGTGTGCYCACTCAGGTCCTGGSGTT-3':

SEQ ID NO: 31
1'-ATGTGGGGAYCGKTTTYAMMCTTTTCAATTG-3':

SEQ ID NO: 32
1'-ATGGAAGCCCCAGCTCAGCTTCTCTTCC-3':

F-set Sense Primer (Mixture of the Following 4 Primers)

SEQ ID NO: 33
1'-ATGAGIMMKTCIMTTCAITTCYTGGG-3':

SEQ ID NO: 34
1'-ATGAKGTHCYCIGCTCAGYTYCTIRG-3':

SEQ ID NO: 35
1'-ATGGTRTCCWCASCTCAGTTCCTTG-3':

SEQ ID NO: 36
1'-ATGTATATATGTTTGTTGTCTATTTCT-3':

G-set Sense Primer (Mixture of the Following 4 Primers)

SEQ ID NO: 37
1'ATGAAGTTGCCTGTTAGGCTGTTGGTGCT-3':

SEQ ID NO: 38
1'-ATGGATTTWCARGTGCAGATTWTCAGCTT-3':

SEQ ID NO: 39
1'-ATGGTYCTYATVTCCTTGCTGTTCTGG-3':

SEQ ID NO: 40
1'-ATGGTYCTYATVTTRCTGCTGCTATGG-3':

KVL Antisense Primer

SEQ ID NO: 41
ACTGGATGGTGGGAAGATGGA:

B. Primers for use in PCR Amplification of a Gene Encoding Mouse H-chain V-region The following two primer sets were employed 4-set primers having, at the 5' end, a homology to the mouse H-chain signal part and a primer having, at the 3' end, a homology to the IGHC part; and 1-set primers having, at the 5' end, a homology to the FR1 part and 2-set primers having, at the 3' end, a homology to the mouse H-chain constant region (IGHC). Polymerase chain reaction was performed by use of the two primer sets, whereby a mouse immunoglobulin H-chain variable region DNA fragment was isolated from the cDNA. The primer sequences are as follows.

(i) Primers for Mouse H-chain Variable Region Cloning VH Sense (Signal Part: 4-set Primers)

These primers were synthesized according to Current Protocols in Immunology (John Wiley and Sons, Inc.), Unit 2.12 Cloning, Expression, and Modification of Antibody V Regions (Table 2.12.2).

SEQ ID NO: 42
5'-ATG GRA TGS AGC TGK GTM ATS CTC TT-3'
(degeneracy: 32):

SEQ ID NO: 43
5'-ATG RAC TTC GGG YTG AGC TKG GTT TT-3'
(degeneracy: 8):

SEQ ID NO: 44
5'-ATG GCT GTC TTG GGG CTG CTC TTC T-3':

SEQ ID NO: 45
5'-ATG GRC AGR CTT ACW TYY-3' (degeneracy: 32):

(ii) Primers for Mouse H-chain Variable Region Cloning VH Sense (FR1 Part)

These primers were designed by nucleotide sequence modification of sense primers disclosed in a document (Tan et al, "Superhumanized" Antibodies: Reduction of Immunoogenic Potential by Complementarity-Determining Region Grafting with Human Germline Sequences: Application to an Anti-CD281, Journal of Immunology 169 (2002), p. 1119-1125).

SEQ ID NO: 46
1'-SAG GTS MAR CTK SAG SAG TCW GG-3'
(degeneracy: 256):

VH Antisense (Antisense Primer Common to 3 and 4)

The primer was designed through degeneration of the nucleotide sequence so that the primer can be annealed with all the isoforms of mouse IgG.

SEQ ID NO: 47
5'-CAS CCC CAT CDG TCT ATC C-3' (degeneracy: 6):

Example 5

Production of Chimera Anti-CDH3 Immunoglobulin Expression Vector

Production of Expression Plasmid

Through PCR employing DNA Engine (Peltier Thermal Cycler, MJ Research, Bio-Rad), each variable region of the L-chain and the H-chain of an anti-CDH3 mouse monoclonal antibody was amplified by use of the primers described in Example 4. Each of the thus-amplified DNA fragments was incorporated into a sub-cloning vector pGEM (product of Promega). The nucleotide sequence of the DNA fragment was determined by use of a universal primer which binds to T7 and SP6 promoter of the vector. The thus-obtained nucleotide sequences of the L-chain and H-chain variable regions of the anti-CDH3 antibody were searched by IMGT/V-QUEST Search page (http://imgt.cines.fr/IMGT_vquest/vquest?livret=0&Option=mouseIg), whereby completion of cloning of the antibody genes was confirmed.

Next, a gene encoding the human Cκ region was linked to the cloned gene encoding the V region of the L-chain of the anti-CDH3 antibody, and a gene encoding the human Cγ1 region was linked to the gene encoding the V region of the H-chain. The thus-designed L-chain and H-chain chimeric antibody genes were synthesized in full length by GenScript. At the time, frequency of codon usage was optimized so as to obtain efficient gene expression in producing cells (according to a method disclosed in Kim et al., Codon optimization for high-level expression of human erythropoietin (EPO) in mammalian cells, Gene, 199, 1997, p. 293-301). Specifically, in the case of L-chain, for the purpose of effective translation, an essential DNA sequence (Kozak, M., J., At least six nucleotides preceding the AUG initiator codon enhance translation in mammalian cells. J. Mol. Biol. 196, p. 947-950, 1987), signal peptide of mouse IGKV, the V region of the L-chain of the anti-CDH3 antibody, and the human Cκ region were juxtaposed in this order, and restriction enzyme sites were added to both ends (NheI on the 5' side and EcoRI on the 3' side). The chimera H-chain was prepared in the same manner. Each of the synthesized genes was cut with NheI and EcoRI, and the cut fragment was incorporated into an expression vector pCAGGS between the NheI site and the EcoRI site, to thereby produce an anti-CDH3 chimeric antibody L-chain expression vector pCAGGS-IGK and H-chain expression vector pCAGGS-IGH.

Example 6

Production of Chimera Anti-CDH3 Immunoglobulin stable expression vector

For realizing high-level expression of a genetically modified antibody gene in CHO cells, there was produced an expression vector into which a dihydrofolate reductase (dhfr) gene linked to a CMV promoter sequence and having poly A signal had been incorporated.

For producing a chimeric antibody-stably expressing/producing cell line, there was produced a pCAGGS expression vector into which a dhfr gene had been incorporated. Specifically, into pCAGGS-IGH and pCAGGS-IGK, which are transient expression vectors, a dhfr gene having a CMV promoter and poly A signal was incorporated. Each of a mouse dhfr gene having a CMV promoter and a Kozak sequence and SV40 poly A signal was amplified through PCR. These genes in mixture form were linked together through PCR, and an HindIII site was added to both ends of the linked product, to thereby acquire a gene fragment of HindIII-CMV promoter-Kozak-dhfr-poly A-HindIII. The fragment was inserted into pCAGGS-IGH or pCAGGS-IGK at the HindIII sites, to thereby obtain pCAGGS-IGH-CMVp-dhfr-A and pCAGGS-IGK-CMVp-dhfr-A. These expression vectors enable chimeric antibody expression with a CAG promoter, and expression of a dhfr gene with a CMV promoter, whereby a chimeric antibody can be effectively produced through gene amplification.

Example 7

Establishing a Chimera Anti-CDH3-producing CHO Cell Line

CHO dhfr cells (G. Urlaub et al., Isolation of Chinese hamster cell mutants deficient in dihydrofolate reductase activity, Proc. Natl. Acad. Sci. USA 77, p. 4216-4220, 1980) were simultaneously transformed by use of two plasmids (linear plasmids obtained by cutting circular plasmids with PvuI in an ampicillin-resistant gene); i.e., a pCAGGS-IGK-CMV-dhfr-A vector for chimera anti-CDH3 L chain expression and a pCAGGS-IGH-CMV-dhfr-A vector for chimera anti-CDH3 H chain expression. Electroporation was performed by means of Amaxa (product of Lonza). DNA fragment (2 μg/sample; in the case of L-chain plasmid or H-chain plasmid) was added to a 0.1 mL Amaxa electroporation CHO buffer containing $3\times10^3$ cells and a pulse was applied.

The cells which had undergone electroporation were added to an Iscove's Modified Dulbecco medium (IMDM: free of HT) containing 10% dialyzed FBS that is free of HT (H: hypoxanthine, T: thymidine). Three days after transfection, the medium was changed to an IMDM medium free of 10% dialyzed FBS, 2 mM L-glutamine, and HT, and neo+ transformed cells were selected by use of 1 mg/mL G418, to thereby acquire clones of a chimeric antibody-producing positive cell line. Subsequently, gene amplification was performed by use of the clones selected by using G418. 2-Round amplification was performed in 250 nM and 1,000 nM methotrexate (MTX), and cell lines which can produce a chimera CDH3 antibody (about 50 to 100 mg/L-culture supernatant) were established. The thus established chimera anti-CDH3 antibody-stably expressing CHO cell lines were deposited with Incorporated Administrative Agency, the National Institute of Technology and Evaluation, Patent Microorganisms Depositary.

TABLE 1

| Cell line | Accession No. |
|---|---|
| PPAT-052-02c | NITE BP-1041 |
| PPAT-052-03c | NITE BP-1042 |
| PPAT-052-09c | NITE BP-1043 |
| PPAT-052-21c | NITE BP-1044 |
| PPAT-052-24c | NITE BP-1045 |
| PPAT-052-25c | NITE BP-1046 |
| PPAT-052-26c | NITE BP-1047 |
| PPAT-052-27c | NITE BP-1048 |
| PPAT-052-28c | NITE BP-1049 |
| PPAT-052-29c | NITE BP-1050 |

Example 8

Acquisition of Purified Antibodies

The antibodies were purified from the culture supernatant by use of protein A.

Example 9

Confirmation of Affinity

Through a competitive method, the affinity of the mouse anti-CDH3 antibody was compared with that of the chimera anti-CDH3 antibody. In the competitive method, the affinity of the anti-CDH3 antibody was determined through flow cytometry (BD, FACS Calibur) by use of cancer cells NCI-H358, which are known to be CDH3 high expression cells.

Specifically, an antibody serially diluted sample (400 μg/mL to 24 ng/mL) (50 μL) and an Alexa488-labeld antibody (4 μg/mL) (50 μL) were added to and mixed on a 96-well plate. NCI-H358 cells were removed from a culture plate through treatment with 2 mM EDTA-PBS, and the cells were suspended in an FACS solution (1% BSA PBS) to a concentration of $1.5\times10^6$/mL. An aliquot (100 μL) of the suspension was added to the wells containing the antibody mixture. After addition, reaction was performed at room temperature for 60 minutes, and the plate was washed twice with an FACS solution (200 μL/well). Subsequently, the fluorescence intensity (GEO mean) of each well was determined through flow cytometry.

The percent of binding inhibition of the Alexa488-labeled antibody was calculated from a GEO mean value, as compared with that obtained by the reaction only with the Alexa488-labeld antibody (1 μg/mL). The antibody concentration showing 50% inhibition was calculated, and the data were compared.

FIG. 1 shows the affinity evaluation of PPMX2016 (mouse antibody) and PPAT-052-27c (chimeric antibody thereof). Virtually no difference in affinity was observed between the two antibodies.

Example 10

Production of Labeled Antibodies (1) Bonding DOTA to antibody

An antibody was dissolved in a buffer (50 mM Bicine-NaOH, 150 mM NaCl, pH: 8.5) to an antibody concentration of 10 mg/mL. Separately, isothiocyanobenzyl DOTA (B-205, product of Macrocyclics) was dissolved in DMSO to a concentration of 10 mg/mL. The two solutions were mixed together so as to adjust the ratio by mole of antibody to DOTA 1:1 (adding ratio 1:1), 1:3 (adding ratio 1:3), or 1:10 (adding ratio 1:10), and the mixture was stirred and allowed to stand at 25° C. for 17 hours. After termination of reaction, the reaction mixture was purified by means of a desalting column (PD-10, product of GE Healthcare, 17-0435-01) with PBS. The following antibodies were used: PPMX2016, PPMX2025, PPMX2029, PPAT-052-27c, and PPAT-052-28c.

(2) Determination of Percent of Chelate Incorporation

The percent of chelate incorporated into antibody was determined through chelatometric titration. The modification antibody protein concentration was determined through a customary method in advance, and the number of moles of modification antibody was calculated from the molecular weight of IgG. To 1-mg/mL standard copper solution (100 μL) whose concentration had been determined through atomic absorption spectrometry, an arsenazo III reagent (0.776 mg) and metal-free 5M ammonium acetate (product of Sigma Aldrich) solution (3 mL) were added, and ultrapure water was added to the solution to adjust the final volume to 10 mL. The resultant solution was stored at room temperature in the dark to prepare the arsenazo III solution. DOTA was dissolved in ultrapure water, to thereby prepare a DOTA standard solution. A modification antibody was dissolved in ultrapure water, to thereby prepare a modification antibody solution. The DOTA standard solution or the modification antibody solution (10 μL) was admixed with the arsenazo III solution (190 and the mixture was incubated at 37° C. for 30 minutes. Subsequently, the absorbance of the mixture was measured at a wavelength of 630 nm. A standard curve was drawn from the absorbance measurements of DOTA standard solutions. By the standard curve, the number of DOTA molecule(s) bound to the modification antibody was calculated (average number of DOTA modification).

Table 2 shows the results (DOTA-adding ratio and actual average number of modifying DOTA). As is clear from Table 2, the number of DOTA molecules bound to the antibody was found to be determined by the adding ratio of DOTA.

TABLE 2

| Antibody to DOTA-adding ratio | Av. no. of modifying DOTA |
|---|---|
| PPMX2025 (adding ratio 1:1) | 0.9 |
| PPMX2025 (adding ratio 1:3) | 2.0 |
| PPMX2025 (adding ratio 1:10) | 5.3 |
| PPMX2016 (adding ratio 1:1) | 0.7 |

TABLE 2-continued

| Antibody to DOTA-adding ratio | Av. no. of modifying DOTA |
|---|---|
| PPMX2016 (adding ratio 1:3) | 2.1 |
| PPMX2016 (adding ratio 1:10) | 5.2 |
| PPAT-052-27c (addding ratio 1:3) | 1.8 |

(Note)
PPAT-052-27c was tested only at an adding ratio of 1:3.

(3) Preparation of $^{67}$Ga-, or $^{90}$Y-labeld Antibodies (i) Labeling with $^{67}$Ga or $^{111}$In Each of the purified PPMX2016, PPMX2025, PPMX2029, and PPAT-052-27c antibodies and PPAT-052-28c antibody was dissolved in a buffer (0.25M ammonium acetate-HCl, pH: 5.5) to a concentration of 6 mg/mL. A $^{67}GaCl_3$ solution (product of Fuji Film RI Pharma) or a $^{111}InCl_3$ solution (product of MDS Nordion Inc.) was added to the antibody solution, and the mixture was incubated at 45° C. for one hour.

(ii) Labeling with $^{90}$Y

Each of the purified PPMX2029 and PPAT-052-27c antibodies was dissolved in a buffer (0.25M ammonium acetate-HCl, pH: 5.5) to a concentration of 6 mg/mL. A $^{90}YCl_3$ solution (product of Nuclitec) was added to the antibody solution, and the mixture was incubated at 45° C. for one hour.

(iii) Determination of Percent of Labeling

An aliquot of the labeling reaction mixture was sampled and subjected to thin-layer chromatography (61885, product of PALL), to thereby determine the percent of labeling. Physiological saline was employed as an eluent, and the radioactivity was measured at the top and bottom ends of a strip by means of a γ-counter. The percent of labeling was calculated by the following equation.

$$\text{Percent of labeling}=(\text{bottom end count}/(\text{top end count}+\text{bottom end count}))\times 100\ (\%) \quad [E1]$$

When the percent of labeling reached 90% or higher, the labeled antibody was used in the subsequent experiment. The labeled antibodies were purified a desalting column (PD-10, product of GE Healthcare, 17-0435-01) with PBS.

Example 11

Investigation of Relationship Between Percent of Chelate- Incorporation and Bio-distribution (i.e., Distribution in the Body)

PPMX2016, PPMX2025, and PPMX2029 were investigated in terms of bio-distribution by virtue of difference of percent of chelate incorporation values (DOTA-adding ratio 1:1, 1:3, and 1:10).

Firstly, NCI-H358 was cultured in a 10% FBS-containing RPMI1640 medium, and the cultured cells were subcutaneously transplanted to the right ventral region of each of the nude mice (female, 7-week old, CLEA Japan Inc.) at a cell concentration of $1\times10^7$ cells/mouse. The mice were bred until the average tumor volume reached 100 to 150 $mm^3$.

Then, to the NCI-H358-transplanted mice, $^{67}$Ga-DOTA-PPMX2016 antibody (adding ratio 1:3 and 1:10), $^{67}$Ga-DOTA-PPMX2025 antibody (adding ratio 1:3 and 1:10), or $^{67}$Ga-DOTA-PPMX2029 antibody(adding ratio 1:3 and 1:10) was administered at a dose of 370 kBq/mouse.

Ninety-six hours after administration, the mice were sacrificed to anatomy, and tissues and the tumor were removed. The weight of each tissue and the tumor weight were measured, the radioactivity was measured by means of a 7-counter and % ID/g was calculated by the following equation.

% ID/g=(accumulated RI amount/total administered RI amount×100(%))/weight (g) [E2]

FIGS. 2 to 7 show the results. All the tested antibodies exhibited enhanced accumulation in the tumor, at a DOTA-adding ratio of 1:3, as compared with the case at a ratio of 1:10. Such enhanced accumulation results in enhancement of therapeutic effect. In addition, adverse side effects, which would otherwise be caused by retention of a radioactive substance in non-targeted organs, can be avoided.

Figure 8:
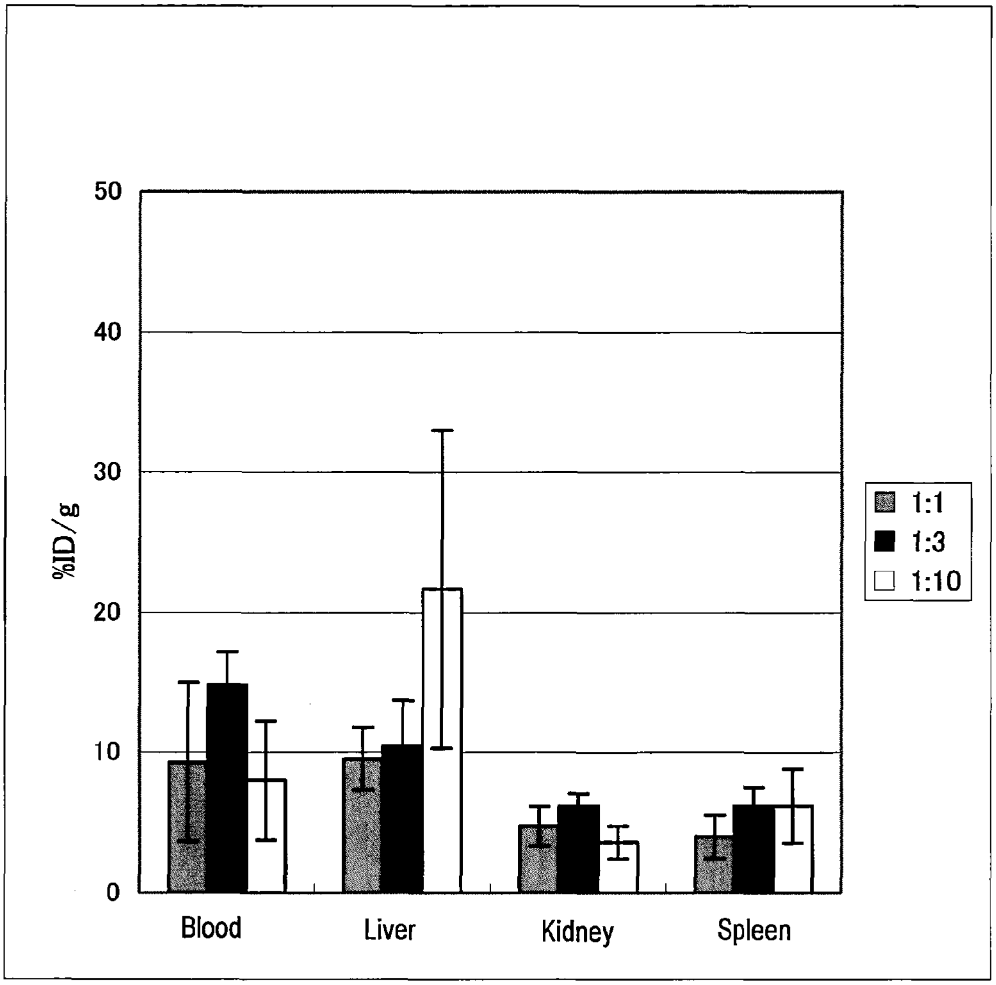
[FIG. 8] Bio-distribution of $^{67}$Ga-DOTA-PPMX2025 antibody in case of the added antibody-DOTA ratios of 1:1, 1:3, and 1:10 96 hours after administration thereof.

FIG. 8 shows the result of administration of $^{67}$Ga-DOTA-PPMX2025 antibody (use ratio 1:1, 1:3, and 1:10) to non-cancer-bearing nude mice (female, 7-week old, CLEA Japan Inc.) at 370 kBq/mouse. The antibody was accumulated highly in the liver when the adding ratio was 1:10, whereas accumulation in the liver was low when the ratio was 1:3 or 1:1, which indicates that adverse side effects such as radioactive damage are prevented on the liver.

Example 12

Investigation of Behavior of Anti-caldina Chimeric Antibody in the Body

The behaviors of chimera antibodies PPAT-052-27c and PPAT-052-28c in the body were investigated.

Firstly, NCI-H1373 was cultured in a 10% FBS-containing RPMI1640 medium, and the cultured cells were subcutaneously transplanted into to the right ventral region of each of the nude mice (female, 9-week old, CLEA Japan Inc.) at a cell concentration of $4\times10^6$ cells/mouse. The mice were bred until the average tumor volume reached 100 to 150 mm$^3$.

Then, to the NCI-H1373-transplaned mice, $^{111}$In-DOTA-PPAT-052-27c (adding ratio 1:3) or $^{111}$In-DOTA-PPAT-052-28c (adding ratio 1:3) at a dose of 370 kBq/mouse.

Fourty-eight or ninety-six hours after administration, the mice were sacrificed to anatomy, and tissues and the tumor were removed. The weight of each tissue and the tumor weight were measured, the radioactivity was measured by means of a γ-counter and % ID/g was calculated.

Figure 9:
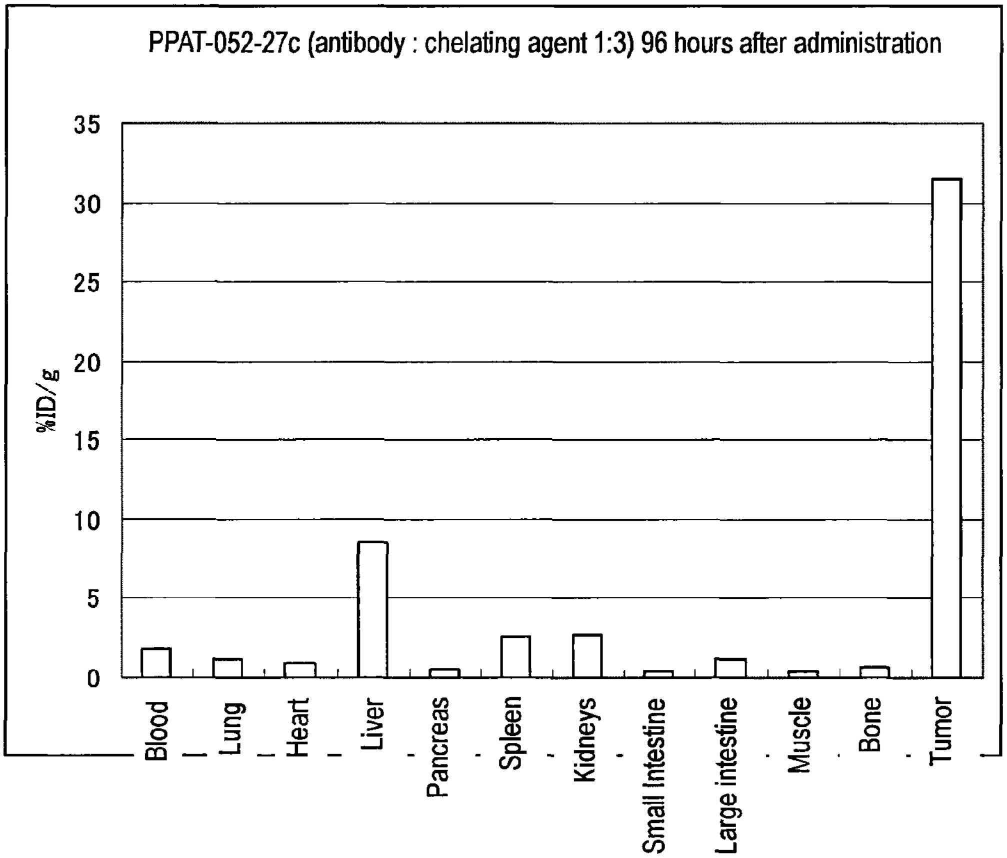
[FIG. 9] Bio-distribution of $^{111}$In-DOTA-PPAT-052-27c antibody (adding ratio of 1:3) 96 hours after administration thereof.
Figure 10:
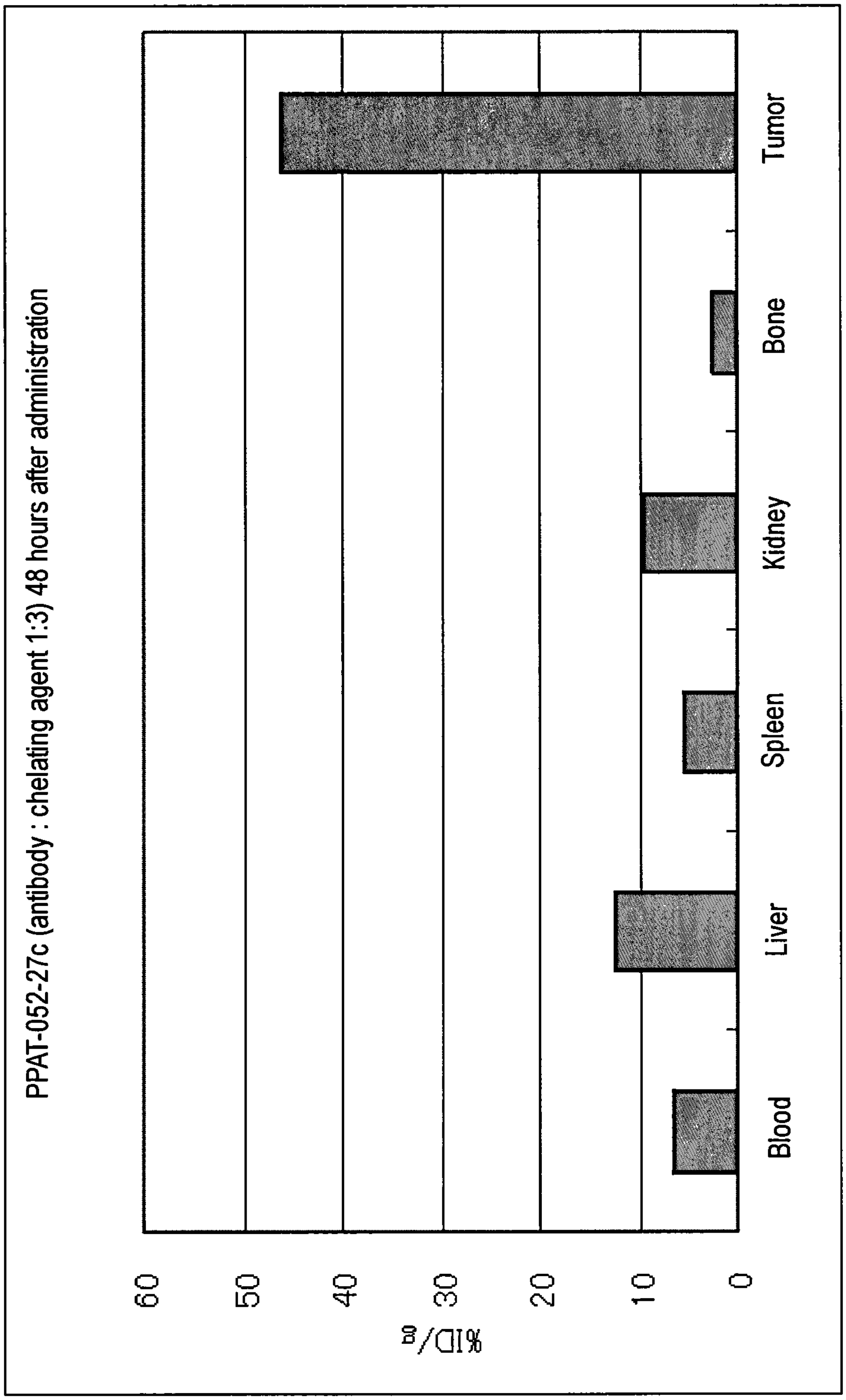
[FIG. 10] Bio-distribution of $^{111}$In-DOTA-PPAT-052-27c antibody (adding ratio of 1:3) 48 hours after administration thereof.
Figure 11:
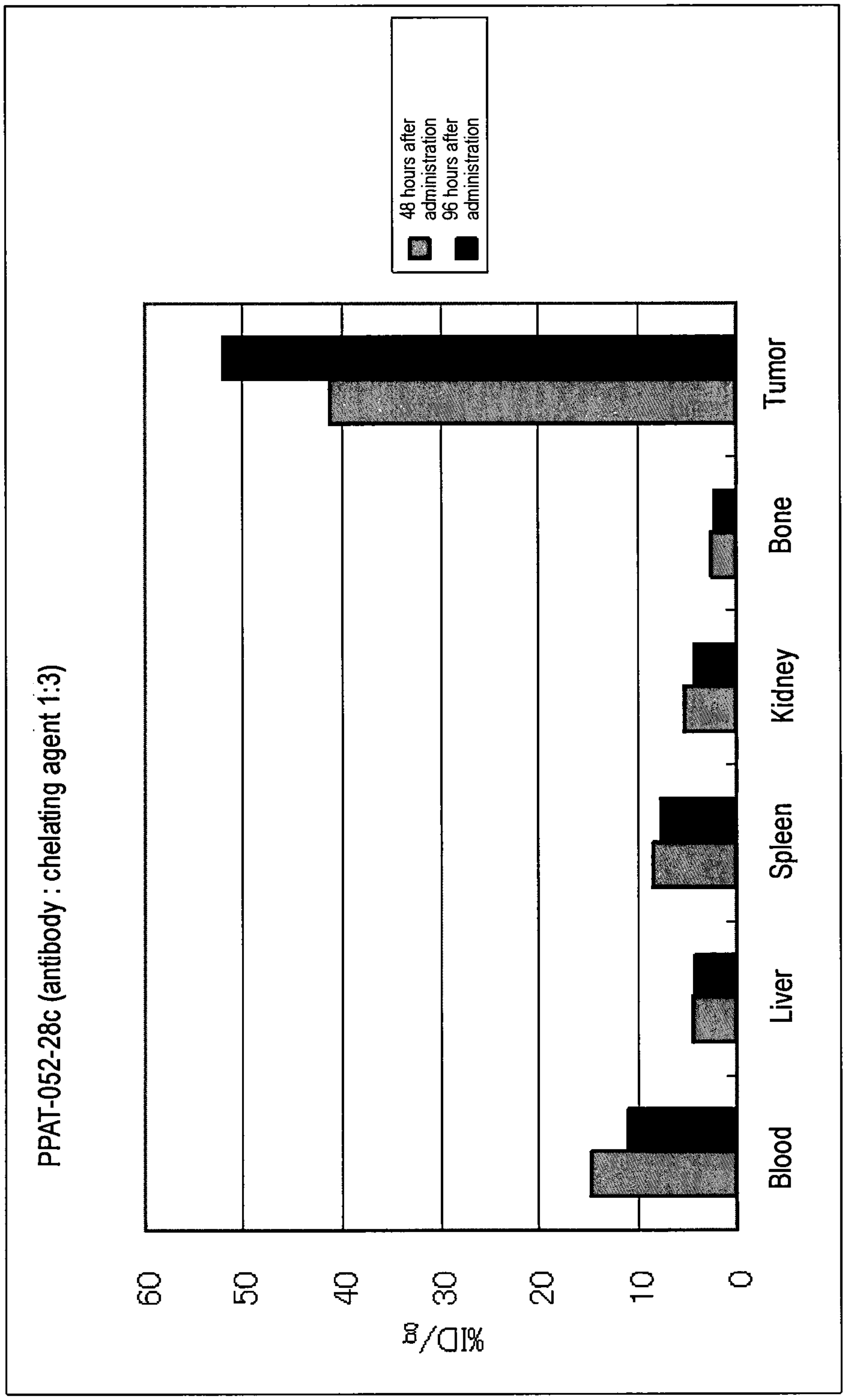
[FIG. 11] Bio-distribution of $^{111}$In-DOTA-PPAT-052-28c antibody (adding ratio of 1:3) 48 hours and 96 hours after administration thereof.

FIGS. 9 to 11 show the results. PPAT-052-27c exhibited a percent accumulation in the tumor as high as 46% ID/g 48 hours after administration. PPAT-052-28c exhibited a percent accumulation in the tumor as high as 41% ID/g 48 hours after administration and 52% ID/g 96 hours after administration.

Example 13

Xenograft Test

NCI-H358 was cultured in a 10% FBS-containing RPMI1640 medium, and the cultured cells were subcutaneously transplanted into to the right ventral region of each of the nude mice (female, 7-week old, CLEA Japan Inc.) at a cell concentration of $1\times10^7$ cells/mouse.

The NCI-H358-transplaned mice were divided into six groups (n=8). $^{90}$Y-DOTA-PPMX2029 antibody (adding ratio 1:3) was administered at a dose of 7.4 MBq/mouse, 5.6 MBq/mouse, 3.7 MBq/mouse, and 1.9 MBq/mouse. As control groups, unlabeled PPMX2029 was administered at a dose of 80 pg/mouse, and physiological saline was administered at a dose of 100 μL/mouse. In all the groups, administration was performed when the average tumor volume reached 100 to 150 mm$^3$.

After administration, the body weight and the tumor volume were measured twice a week (every 3 or 4 days). This observation wad continued to day 51 after administration.

Figure 12:
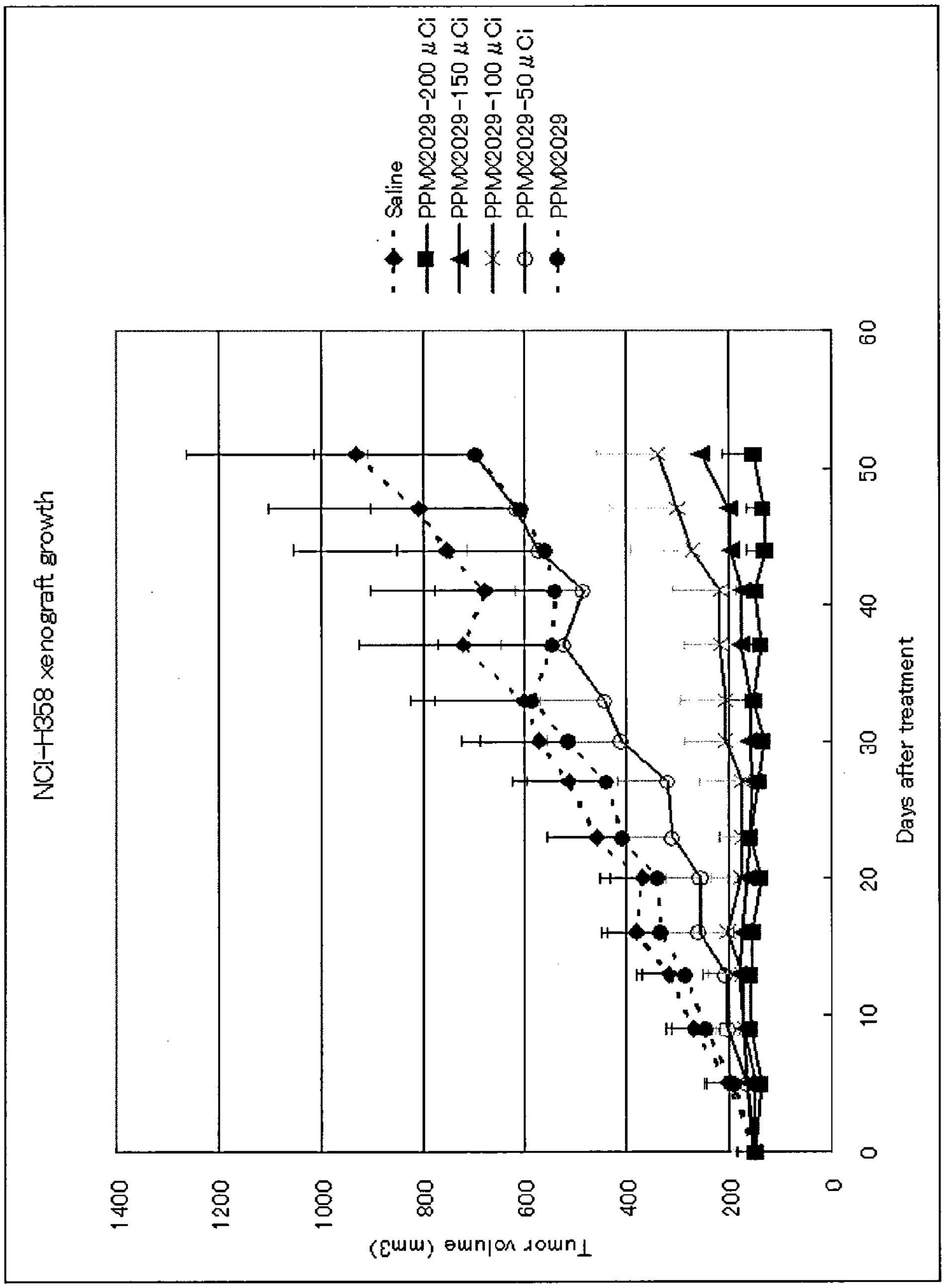
[FIG. 12] Anti-tumor effect of $^{90}$Y-DOTA-PPMX2029 antibody (adding ratio of 1:3) in xenograft model.

FIG. 12 shows the test results. $^{90}$Y-DOTA-PPMX2029 antibody (adding ratio 1:3) exhibited anti-tumor effect proportional to the radioactivity.

Separately, NCI-H1373 was cultured in a 10% FBS-containing RPMI1640 medium, and the cultured cells were subcutaneously transplanted into to the right ventral region of each of the nude mice (female, 7-week old, CLEA Japan Inc.) at a cell concentration of $5\times10^6$ cells/mouse.

The NCI-H1373-transplaned mice were divided into four groups (n=8). $^{90}$Y-DOTA-PPAT-052-27c antibody (adding ratio 1:3) was administered at a dose of 5.6 MBq/mouse and 3.7 MBq/mouse. As control groups, unlabeled PPMX2029 was administered at a dose of 60 μg/mouse, and physiological saline was administered at a dose of 100 μL/mouse. In all the groups, administration was performed when the average tumor volume reached 100 to 150 mm$^3$.

After administration, the body weight and the tumor volume were measured twice a week (every 3 or 4 days). This observation wad continued to day 26 after administration.

Figure 13:
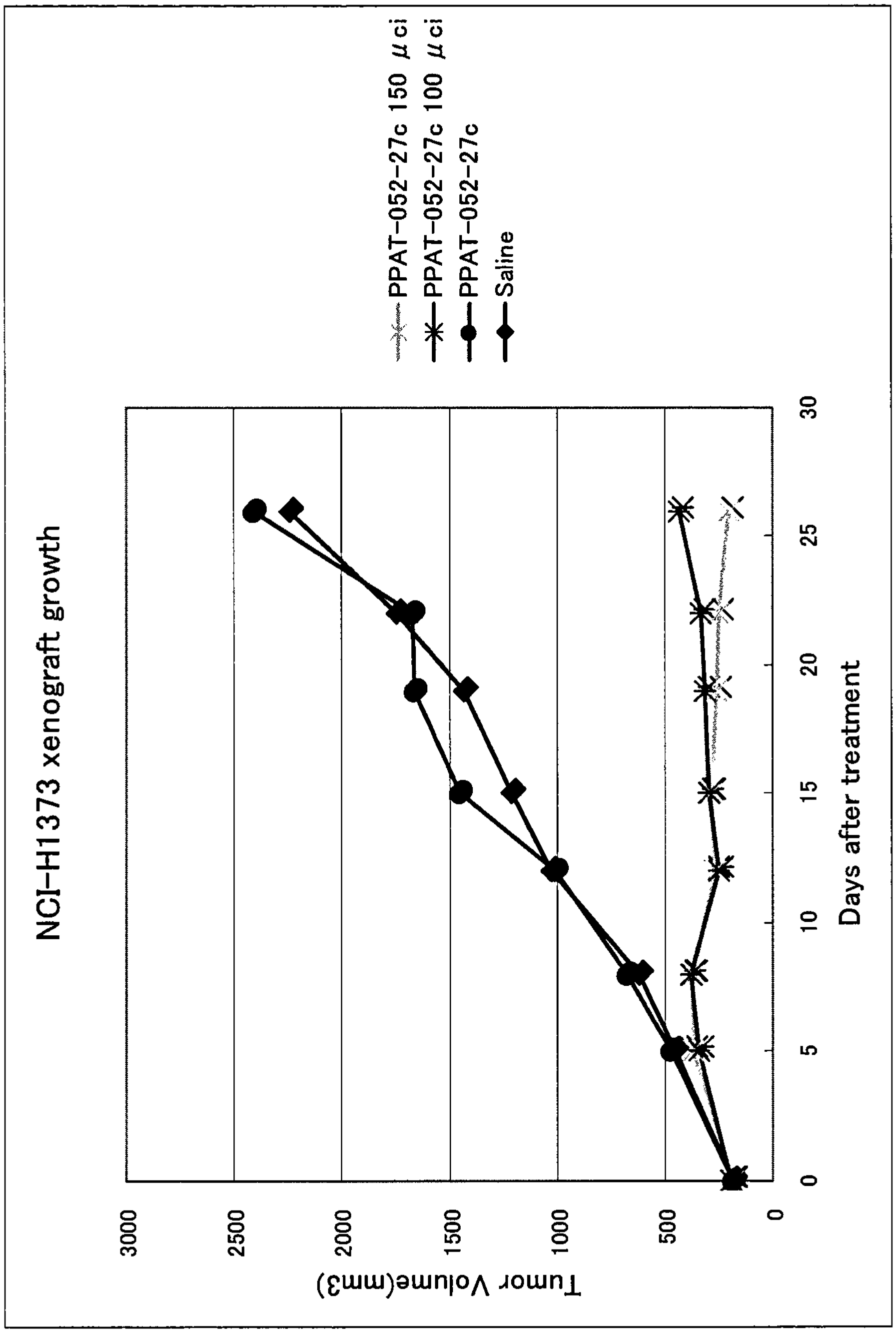
[FIG. 13] Anti-tumor effect of $^{90}$Y-DOTA-PPAT-052-27c antibody (adding ratio of 1:3) in xenograft model.

FIG. 13 shows the test results. $^{90}$Y-DOTA-PPAT-052-27c (adding ratio 1:3) exhibited anti-tumor effect proportional to the radioactivity.

Example 14

Immunohistochemical Staining

CDH3 protein expression in a clinical cancer specimen was confirmed by immunohistochemical staining of a cancer specimen tissue array.

As cancer specimen tissue arrays, employed were tissues of pancreatic cancer (adenocarcinoma), lung cancer (adenocarcinoma), lung cancer (squamous cell carcinoma), and colorectal cancer (adenocarcinoma), which are the products of Shanghai Outdo Biotech Co., Ltd.

Each tissue array slide was dewaxed and activated with 10 mM Tris 1 mM EDTA (pH: 9.0) at 95° C. for 40 minutes. Endogenous peroxidase in the array slide was inactivated with a blocking agent, which is included in the ENVISION+ Kit (product of Dako). Subsequently, the tissue array slide was reacted with 5 μg/mL anti-CDH3 antibody 610227 (product of BD BIOSCIENCE) or with 5 μg/mL anti-HBs antibody Hyb-3423 (negative control) at 4° C. overnight. The antibody solution was washed out, and the tissue array slide was further reacted with a polymer secondary antibody reagent which is included in the ENVISION+Kit at room temperature for 30 minutes. The slide was then color-developed by a coloring reagent which is included in the ENVISION+Kit, and nuclear staining was performed by use of a hematoxylin/eosin solution.

Figure 14:
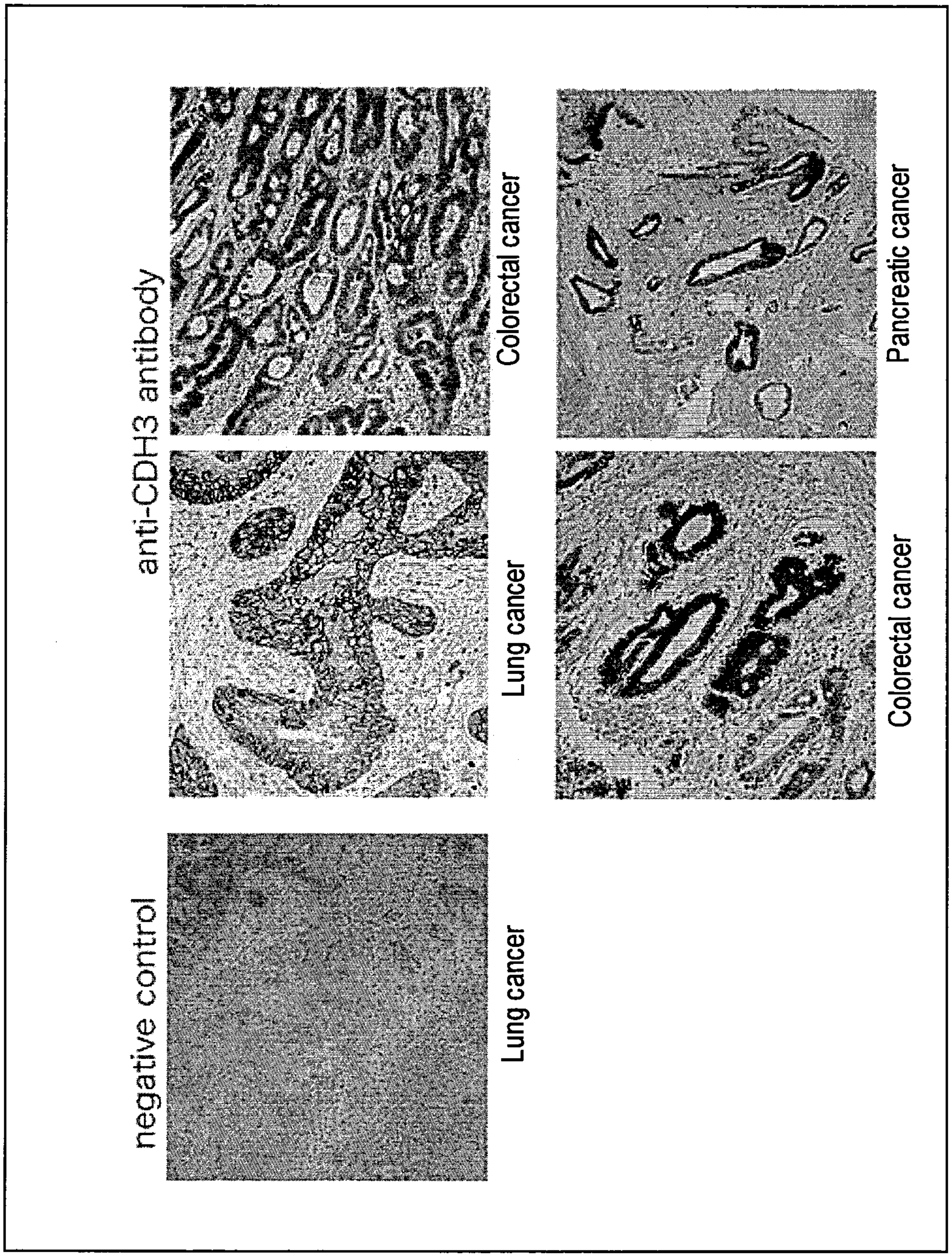
[FIG. 14] Photoimages showing the results of immunohistochemical staining for confirming CDH3 protein expression.

FIG. 14 shows the results. Cancer cells were stained by anti-CDH3 antibody, but normal cells were not stained.

The invention claimed is:

1. A radioactive metal-labeled anti-p-cadherin antibody, obtained by a process comprising binding a radioactive metallic element to an anti-p-cadherin antibody via a metal-chelating reagent, wherein the anti-p-cadherin antibody is a monoclonal antibody produced by an antibody-producing cell of an accession number of NITE BP-897, NITE BP-898, NITE BP-899 or NITE BP-1040, or a recombinant antibody thereof or a chimeric antibody thereof or a humanized antibody thereof.

2. The radioactive metal-labeled anti-p-cadherin antibody of claim 1, wherein the anti-p-cadherin antibody is a monoclonal antibody, produced by an antibody-producing cell of an accession number of NITE BP-897, NITE BP-898, NITE BP-899, NITE BP-1040, NITE BP-1044, NITE BP-1048, NITE BP-1049, or NITE BP-1050, or a recombinant antibody thereof.

3. The radioactive metal-labeled anti-p-cadherin antibody of claim 1, wherein the metal-chelating reagent is selected from the group consisting of isothiocyanobenzyl DOTA, methylisothiocyanobenzyl DTPA, and cyclohexylisothiocyanobenzyl DTPA.

4. The radioactive metal-labeled anti-p-cadherin antibody of claim 1, wherein a mole ratio of the anti-p-cadherin antibody to the metal-chelating reagent is from 1:0.1 to 1:4.5.

5. The radioactive metal-labeled anti-p-cadherin antibody of claim 4, wherein the mole ratio of the anti-p-cadherin antibody to the metal-chelating reagent is from 1:0.5 to 1:3.

6. The radioactive metal-labeled anti-p-cadherin antibody of claim 1, wherein the radioactive metallic element is a cytotoxic radioactive metal suitable for treating a p-cadherin expressing cancer.

7. The radioactive metal-labeled anti-p-cadherin antibody of claim 6, wherein the cytotoxic radioactive metal is selected from the group consisting of yttrium-90 ($^{90}Y$), rhenium-186 ($^{186}Re$), rhenium-188 ($^{188}Re$), copper-67 ($^{67}Cu$), iron-59 ($^{59}Fe$), strontium-89 ($^{89}Sr$), gold-198 ($^{198}Au$), dysprosium-165 ($^{165}Dy$), ruthenium-103 ($^{103}Ru$), holmium-166 ($^{166}Ho$), samarium-153 ($^{153}Sm$), and lutetium-177 ($^{177}Lu$).

8. The radioactive metal-labeled anti-p-cadherin antibody of claim 6, wherein the cytotoxic radioactive metal is yttrium-90 ($^{90}Y$).

9. The radioactive metal-labeled anti-p-cadherin antibody of claim 6, wherein the cancer therapy is suitable for treating a p-cadherin-expressing cancer.

10. The radioactive metal-labeled anti-p-cadherin antibody of claim 1, wherein the radioactive metallic element is a non-cytotoxic radioactive metal suitable for diagnosing p-cadherin expressing cancer.

11. The radioactive metal-labeled anti-p-cadherin antibody of claim 10, wherein the non-cytotoxic radioactive metal is selected from the group consisting of technetium-99m ($^{99m}$Tc), indium-111 ($^{111}$In), indium-113m ($^{113m}$In), gallium-67 ($^{67}$Ga), gallium-68 ($^{68}$Ga), thallium-201 ($^{201}$T1), cobalt-57 ($^{57}$Co), strontium-85 ($^{85}$Sr), and copper-64 ($^{64}$Cu).

12. The radioactive metal-labeled anti-p-cadherin antibody of claim 10, wherein the non-cytotoxic radioactive metal is indium-111 ($^{111}$In) or copper-64 ($^{64}$Cu).

13. A p-cadherin expressing cancer therapeutic agent comprising, as an active ingredient, the radioactive metal-labeled anti-p-cadherin antibody of claim 6.

14. A p-cadherin expressing cancer diagnostic agent comprising, as an active ingredient, the radioactive metal-labeled anti-p-cadherin antibody of claim 10.

15. An antibody-producing cell deposited as an accession number of NITE BP-897, NITE BP-898, NITE BP-899, NITE BP-1040, NITE BP-1044, NITE BP-1048, NITE BP-1049, or NITE BP-1050.

16. A metal chelating reagent-binding anti-p-cadherin antibody, obtained by a process comprising binding a metal-chelating reagent to an anti-p-cadherin antibody, wherein the anti-p-cadherin antibody is a monoclonal antibody produced by an antibody-producing cell of an accession number of NITE BP-897, NITE BP-898, NITE BP-899, or NITE BP-1040, or a recombinant antibody thereof or a chimeric antibody thereof or a humanized antibody thereof.

17. The metal-chelating reagent-binding anti-p-cadherin antibody of claim 16, wherein the anti-p-cadherin antibody is a monoclonal antibody produced by an antibody-producing cell of an accession number of NITE BP-897, NITE BP-898, NITE BP-899, NITE BP-1040, NITE BP-1044, NITE BP-1048, NITE BP-1049, or NITE BP-1050, or a recombinant antibody thereof.

18. The metal-chelating reagent-binding anti-p-cadherin antibody of claim 16, wherein the metal-chelating reagent is selected from the group consisting of isothiocyanobenzyl DOTA, methylisothiocyanobenzyl DTPA, and cyclohexyl-isothiocyanobenzyl DTPA.

19. The metal-chelating reagent-binding anti-p-cadherin antibody of claim 16, wherein a mole ratio of the anti-p-cadherin antibody to the metal-chelating reagent is from 1:0.1 to 1:4.5.

20. The metal-chelating reagent-binding anti-p-cadherin antibody of claim 19, wherein the mole ratio of the anti-p-cadherin antibody to the metal-chelating reagent is from 1:0.5 to 1:3.

21. An anti-p-cadherin antibody which is a monoclonal antibody produced by an antibody-producing cell of an accession number of NITE BP-897, NITE BP-898, NITE BP-899, or NITE BP-1040, or a recombinant antibody thereof or a chimeric antibody thereof or a humanized antibody thereof.

22. An anti-p-cadherin antibody which is a monoclonal antibody produced by an antibody-producing cell of an accession number of NITE BP-897, NITE BP-898, NITE BP-899, NITE BP-1040, NITE BP-1044, NITE BP-1048, NITE BP-1049, or NITE BP-1050 or a recombinant antibody thereof.

23. A method for treating a p-cadherin expressing cancer, comprising:

administering an effective amount of the radioactive metal-labeled anti-cadherin antibody of claim 6 to a subject in need thereof.

24. A cancer diagnosis method of diagnosing a p-cadherin expressing cancer, comprising:

administering an effective amount of the radioactive metal-labeled anti-cadherin antibody of claim 10 to a subject in need thereof; and diagnosing the p-cadherin expressing cancer.

* * * * *

UNITED STATES PATENT AND TRADEMARK OFFICE

CERTIFICATE OF CORRECTION

PATENT NO. : 8,815,211 B2
APPLICATION NO. : 13/578462
DATED : August 26, 2014
INVENTOR(S) : Akihiro Hino et al.

It is certified that error appears in the above-identified patent and that said Letters Patent is hereby corrected as shown below:

Title Page, Insert --[30] Foreign Application Priority Data
February 10, 2010 [JP] Japan 2010-028028--.

IN THE CLAIMS:

Column 50, Claim 24, line 27, "A cancer diagnosis method of diagnosing a p-cadherin"
should read
--A method of diagnosing a p-cadherin--.

Signed and Sealed this
Third Day of February, 2015

Michelle K. Lee

Michelle K. Lee
*Deputy Director of the United States Patent and Trademark Office*